(12) United States Patent
White et al.

(10) Patent No.: US 7,338,455 B2
(45) Date of Patent: Mar. 4, 2008

(54) METHOD AND APPARATUS FOR DIAGNOSING SCHIZOPHRENIA AND SCHIZOPHRENIA SUBTYPE

(75) Inventors: Keith D. White, Gainesville, FL (US); John M. Kuldau, Gainesville, FL (US); Christiana M. Leonard, Gainesville, FL (US); John Douglas Pettigrew, Taringa (AU)

(73) Assignee: The University of Queensland, Queensland (AU)

( * ) Notice: Subject to any disclaimer, the term of this patent is extended or adjusted under 35 U.S.C. 154(b) by 311 days.

(21) Appl. No.: 10/491,020

(22) PCT Filed: Mar. 25, 2002

(86) PCT No.: PCT/AU02/00348

§ 371 (c)(1),
(2), (4) Date: Oct. 18, 2004

(87) PCT Pub. No.: WO03/026500

PCT Pub. Date: Apr. 3, 2003

(65) Prior Publication Data

US 2005/0079636 A1    Apr. 14, 2005

(30) Foreign Application Priority Data

Sep. 25, 2001    (AU) .................................. 76084/01

(51) Int. Cl.
*A61B 5/16*    (2006.01)
(52) U.S. Cl. ...................................... 600/558
(58) Field of Classification Search ................ 600/558, 600/300, 544, 545; 607/45
See application file for complete search history.

(56) References Cited

U.S. PATENT DOCUMENTS 5,852,489 A    12/1998    Chen
6,629,935 B1    10/2003    Miller et al.

FOREIGN PATENT DOCUMENTS

WO    WO 99/63889    12/1999

OTHER PUBLICATIONS

B.R. Sappenfield et al, Validities of Three Visual Tests for Differentiating Organics from Schizophrenics and Normals, 1961, Journal of Clinical Psychology, 17, 276-278.*

(Continued)

*Primary Examiner*—Max F. Hindenburg
*Assistant Examiner*—Sharick Naqi
(74) *Attorney, Agent, or Firm*—Fulwider Patton LLP

(57) ABSTRACT

A method and apparatus for diagnosing schizophrenia, schizophrenia disorder subgroup, or predisposition thereto in a test subject is disclosed. The method includes the steps of determining an interhemispheric switch rate of the test subject. In one embodiment, the interhemispheric switch rate of the test subject is under conditions of increasing rate of dichoptic reversal, and comparing the switch rate with a corresponding reference switch rate to diagnose presence or absence of schizophrenia, a schizophrenic disorder subgroup, or predisposition thereto. In a preferred embodiment, the interhemispheric switch rate is determined by measuring the rate of binocular rivalry in the test subject. Also disclosed is use of a diagnostic method in genetic linkage studies for the identification of the molecular defect(s) underlying schizophrenia, and for the identification of compounds which may alleviate the disorder.

24 Claims, 16 Drawing Sheets

OTHER PUBLICATIONS

Simon A. Surguladze et al., Audio-visual speech perception in schizophrenia: an fMRI study,Feb. 2001, Psychiatry Research, 106(1), 1-14.*

Mary Best and Jonathan B. Demb[1,2CA], Normal Planum Temporale Asymmetry in Dyslexics with a Magnocellular Pathway Deficit; , *NeuroReport 10*, 607-612 (1999); vol. 10, No. 3; Feb. 25, 1999.

Randolph Blake and Nikos K. Logothetis; Visual Competition; *Nature Reviews/Neuroscience*; vol. 3; Jan. 1, 2002.

Randolph Blake; A Neural Theory of Binocular Rivalry, *Psychological Reivew*; vol. 96, No. 1, 145-167; 1989.

Randolph Blake; A Primer on binocular Rivalry, Including current Controversies; *Brain and Mind 2*; 5-38; 2001.

Gary G. Briggs and Robert D. Nebes; Patterns of Hand Preference in a Student Population; *Cortex*; 11, 230-238; 1975.

Pamela D. Butler, PH.D., et al.; Dysfunction of Early-Stage Visual Processing in Schizophrenia; *Am J Psychiatry*; 158:7, Jul. 2001.

Kristin S. Cadenhead et al.; Transient Versus Sustaned Visual Channels in the Visual Backward Masking Deficits of Schizophrenia Patients; *Society of Biological Psychiatry*; pp. 132-138; 1998.

Robert Campain and Jeff Minckler; A Note of the Gross Configurations of the Human Auditory Cortex; *Academic Press, Inc.*; pp. 319-323; 1976.

John B. Carroll; Human Cognitive Abilities, a survey of factor-analytic studies; *Cambridge University Press*; 1993.

Yue Chen et al.; Psychophysical isolation of a motion-processing deficit in schizophrenics and their relatives and its association with impaired smooth pursuit; *Proc. Natl. Acad. Sci. USA*; vol. 96; pp. 4724-4729; Apr. 1999.

Yue Chen; et al.; Motion Perception in Schizophrenia; *Arch Gen. Psychiatry*; vol. 56; Feb. 1999.

Anne L. Foundas et al.; Planum Temporale Asymmetry and Lanagun Dominance; *Neuropsychologia*; vol. 32, No. 10; pp. 1225-1231; 1994.

Anne L. Foundas, M.D. et al.; Morphologic Cerebral Asymmetries and handedness; *Arch Neurol*; vol. 52; May 1995.

Michael F. Green, PhD. et al.; Backward Masking Performance in Unaffected siblings of Schizophrenic Patient; *Arch Gen. Psychiatry*; vol. 54; May 1997.

Patricia S. Goldman-Takic; Development of Cortical Circuitry and Cognitive Function; *Child Development*; vol. 58; pp. 601-622; 1987.

Andres Ide et al.; Bifurcation Patterns in the Human Sylvian Fissure; Hemispheric and Sex Differences; *Cerebral Cortex*; Vo. 6, p. 717-725; 1047-3211; Oct. 1996.

Daniel C. Javitt, M.D., PhD. et al.; Deficits in Auditory and Visual Content-Dependent Processing in Schizophrenia; *Arch Gen. Psychiatry*; vol. 67; Dec. 2000.

Peter Jones et al.; Child developmental risk factors for adult schizophrenia in the British 1946 birth cohort; *The Lancet*; vol. 344; Nov. 19, 1994.

Eric L. Krakauer, M.D., PhD. et al.; Schizophrenia and Strabismus; *The Journal of Nervous and Mental Disease*; vol. 183, No. 10; 1995.

A. Lane et al.; The anthropometric assessment of dysmorphic features in schizophrenia as an index of its developmental origins; *Psychological Medicine*; vol. 27, pp. 1155-1164; 1997.

Sang-Hun Lee and Randolph Blake; Rival ideas about binocular rivalry ;*Vision Research*; vol. 39, pp. 1447-1454; 1999.

Jeffrey Lieberman, M.D. et al.; Time Course and Biologic Correlates of Treatment Response in First-Episode Schizophrenia; *Arch Gen. Psychiatry*; vol. 50, May 1993.

Cognitive Neuroscience Society Eighth Annual Meeting (Mar. 25-27, 2001 New York); A supplement of the Journal of Cognitive Neuroscience; cns@dartmouth.edu.

Christiana M. Leonard et al.; Anatomical Risk Factors for Phonological Dyslexia; *Cerebral Cortex*; vol. 11, pp. 148-157, 1047-3211; Feb. 2001.

Christiana M. Leonard et al.; Cumultive Effect of Anatomical Risk Factors for Schizophrenia: An MRI Study; *Society of Biological Psychiatry*; pp. 374-382; 1999.

Christiana M. Leonard[1,2] et al.; normal Variation in the Frequency and Location of Human Auditory Cortex Landmarks. Heschl'Gyrus: Where Is It?; *Cerebral Cortex*; vol. 8, pp. 397-406, 1047-3211; Jul./Aug. 1998.

Christiana M. Leonard, PhD. et al.; Anomalous Cerebral Structure in Dyslexia Revealed With Magnetic Resonance Imaging; *arch Neurol*; vol. 50, pp. 461-469; May 1993.

David A. Leopold & Nikos K. Logothetis; Activity changes in early visual cortex reflect monkeys' percepts during binocular rivalry; *Nature*; vol. 379, pp. 549-553; Feb. 8, 1996.

David A. Leopold and Nikos K. Logothetis; Multistable phenomena; changing views in perception; *Trends in Cognitive Sciences*; vol. 3, No. 7, Jul. 1999.

Ottmar V. Lipp and Steven P. Krinitsky; the effect of repeated prepulse and reflex stimulus presentations on startle prepulse inhibition; *Biological Psychology*; vol. 47, pp. 65-76; 1998.

Barbara K. Lipska, Ph.D., et al.; Postpubertal Emergence of Hyper-responsiveness to Stress and to Amphetamine after Neonatal Excitoxic Hippocampal Damage: A Potential Animal Model of Schizophrenia; *Neuropsychopharmacology*; vol. 9, No. 1, pp. 67-75, 1993.

Yijun Liu[1,2]; The Human Red Nucleus and Lateral Cerebellum in Supporting Roles for Sensory Information Processing; *Human Brain Mapping*; vol. 10, pp. 147-159; 2000.

Margaret S. Livingstone; Physiological and anatomical evidence for a magnocellular defect in developmental dyslexia; *Proc. Natl. Acad. Science USA*; Col. 88, pp. 7943-7947; Sep. 1991.

Nikos K. Logothetis; What is rivaling during binocular rivalry?; *Nature*; vol. 380; pp. 621-624; Apr. 18, 1996.

Erik D. Lumer; Neural Correlates of Perceptual Rivalry in the Human Brain; *Science*; vol. 280; pp. 1930-1934; Jun. 19, 1998.

Steven M. Miller et al.; Interhemispheric switching mediates perceptual rivalry; *Current Biology*; vol. 10, No. 7; pp. 383-392; 2000.

John W. Olney, M.D. and Nuri B. Farber, M.D.; Glutamate Receptor Dysfunction and Schizophrenia; *Arch Gen Psychiatry*; vol. 52; pp. 998-1007; Dec. 1995.

Godfrey D. Pearlson et al.; Lateral Ventricular Enlargement Associated With Persistent Unemployment and Negative Symptoms in Both Schizophrenia and Bipolar Disorder; *Psychiatry Research*; vol. 12, pp. 1-9; 1984.

V.B. Penhune et al.; Interhemispheric Anatomical Differences in Human Primary Auditory Cortex; Probabilistic Mapping and Volume Measurement from Magnetic Resonance Scans; *Cerebral Cortex*; vol. 6; pp. 661-672 and 1047-3211; Sep./Oct. 1996.

John D. Pettigrew; Searching for the Switch; Neural Bases for Perceptual Rivalry Alternations; *Brain and Mind*; vol. 2; pp. 85-118; 2001.

John D. Pettigrew and Steven M. Miller; A "sticky" interhemispheric switch in bipolar disorder?; *The Royal Society*; pp. 2141-2148; 1998.

Alex Polonsky et al.; Neuronal activity in human primary visual cortex correlates with perception during binocular rivalry; *Nature Neuroscience*; vol. 3, No. 11; pp. 1153-1159; Nov. 2000.

Judith M. Rumsey, PhD.; Brain imaging of Reading Disorders; *Journal of the American Academy of Child & Adolescent Psychiatry*; vol. 37(1): p. 12; Jan. 1998.

David S. Shannahoff-Khalsa and F. Eugene Yates; Ultradian Sleep Rhythms of Lateral EEG, Autonomic, and Cardiovascular Activity Are Coupled In Humans; *Intern. J. Neuroscience*; vol. 101; pp. 21-43; 2000.

David L. Sheinberg and Nikos K. Logothetis; Noticing Familiar Objects in Real World Scenes: The Role of Temporal Cortical Neurons in Natural Vision; *The Journal of Neuroscience*; vol. 21(4); pp. 1340-1350; Feb. 15, 2001.

Kenneth N. Sokolski, M.D. et al.; Effects of Substance Abuseon Hallucination Rates and Treatment Responses in Chronic Psychiatric Patients; *Journal of Clinical Psychiatry*; vol. 55:9; Sep. 1994.

Ramesh Srinivasan et al.; Increased Synchronization of Neuromagnetic Responses during Conscious Perception; *The Journal of Neuroscience*; vol. 19(13); pp. 5435-5448; Jul. 1, 1999.

Janice R. Stevens, M.D.; Abnormal Reinnervation as a Basis for Schizophrenia: A Hypothesis; *Arch Gen Psychiatry*; vol. 49; pp. 238-243; Mar. 1992.

Frank Tong and Stephen A. Engel; Interocular rivalry revealed in the human cortical blind-spot representation; *Nature*; vol. 411; pp. 195-199; May 10, 2001.

Frank Tong et al.; Binocular Rivalry and Visual Awareness in Human Extrastriate Cortex; *Neuron*; vol. 21; pp. 753-759; Oct. 1998.

Giulio Tononi; Schizophrenia and the mechanisms of conscious integration; *Brain Research Reviews*; vol. 31; pp. 391-400; 2000.

Thomas W. Weickert, Ph.D. et al.; Cognitive Impairments in Patients With Schizophrenia Displaying Preserved and Compromised Intellect; *Archives of General Psychiatry*; vol. 57; pp. 907-913; Sep. 2000.

Daniel R. Weinberger, M.D. et al.; Evidence of Dysfunction of a Prefrontal-Limbic Network in Schizophrenia: A Magnetic Resonance Imaging and Regional Crebral Blood Flow Study of Discordant Monozygotic Twins; *The American Journal of Psychiatry*; vol. 149(7); p. 890; Jul. 1992.

D.R. Weinberger; Schizophrenia as a Neurodevelopment Disorder; *Schizophrenia*; Chp. 16; pp. 293-323; 1995.

Sandra F. Witelson and Debra L. Kigar; Sylvian Fissure Morphology and Asymmetry in Men and Women: Bilateral Differences in Relation to Handedness in Men; *The Journal of Comparative Neurology*; pp. 323: 326-340; 1992.

Richard W. Woodcock; Woodcock Reading Mastery Tests—Revised; *American Guidance Service, Inc.*; 1987.

Jinhu Xiong et al.; Clustered Pixels Analysis for Functional MRI Activation Studies of the Human Brain; *Human Brain Mapping*; vol. 3; pp. 287-301; 1995.

Efremov VS.; "Functional Asymmetry of the Cerebral Hemispheres During Visual Perception in Schizophrenics With Productive and Negative Symptoms"; printed from internet site on Sep. 4, 2002.

\* cited by examiner

METHOD AND APPARATUS FOR DIAGNOSING SCHIZOPHRENIA AND SCHIZOPHRENIA SUBTYPE

FIELD OF THE INVENTION

THIS INVENTION relates generally to a method for diagnosing schizophrenic disorders. In particular, the present invention relates to a method for diagnosing a sub-type of schizophrenic disorder. The invention also relates to treatment of schizophrenia, for identifying therapeutic compounds for alleviating schizophrenia, and for identifying genetic markers associated therewith.

BACKGROUND ART

Schizophrenia, a major psychosis that cripples the lives of patients and their families, is a brain disease in search of a neuropathological basis. Stevens (Stevens 1992; Stevens 1997) argues that a majority of patients show no signs of developmental damage, and that an uneven course after onset argues for a search for pathophysiologic processes that coincide more closely with onset, progression, or remissions, yet can explain the evidence of brain damage. She proposes that some neuropathological process that precipitates the disease (Olney and Farber 1995) is followed by waves of aberrant reinnervation and pruning. Lieberman and colleagues' (1993) five year prospective study of schizophrenia suggests that there may be a subgroup with subsequent degeneration after the onset of disease. Whatever the final resolution among these positions it seems clear that the brain lesion model that has been so successful in neuropsychology and neurology has less explanatory power in psychiatry.

Binocular rivalry is on a class of phenomena in which an unchanging but ambiguous sensory input leads to dramatic perceptual switches (Blake, 2001). If a horizontal grating is presented to the right eye and a vertical grating to the left, the usual experience by an observer is a quasi-regular, but unpredictable, switching between two mutually exclusive perceptions: a second or two of seeing only horizontal lines followed by a second or two of seeing only vertical lines (Pettigrew and Miller, 1998).

Binocular rivalry was thought to be based on the properties of monocular neurons early in the visual pathway (Blake, 1989), but recent work in monkeys trained to report their perceptual alternations has argued against this interpretation (Logothetis et al., 1996a). The present consensus is that rivalry is a multi-level process that reflects high level perceptual decisions as well as low level sensory activity (Blake, 2002).

Psychiatric interest began when bipolar patients were shown to have a significantly slower perceptual alternation rate, independent of age and medication (Pettigrew and Miller, 1998; International patent publication WO 99/63889, incorporated herein by reference). The altered neural rhythm revealed by binocular rivalry in bipolar patients is also accompanied by alteration of another of their neural rhythms with a period of hours rather than seconds. Considered along with the evidence that the switches of rivalry reflect interhemispheric switching, (Miller et al., 2000), the neural dysrhythmia in bipolar disorder revealed by binocular rivalry may be related to abnormal regulation of the hemispheric asymmetries of mood. Perceptual rivalry may therefore play a role in explaining bipolar disorder as well as in diagnosing it.

A method and apparatus capable of diagnosing a bipolar disorder, is described in WO 99/63889. The method includes the steps of determining an interhemispheric switch rate of a test subject and comparing the switch rate with a corresponding reference switch rate to diagnose presence or absence of a bipolar disorder or predisposition thereto. The apparatus provides a means for measuring a rate of standard binocular rivalry in a test subject.

Dichoptic alternation during binocular rivalry was first described by Logothetis and Leopold (1996) in normal subjects. If complementary patterns being presented to each eye to produce rivalry are swapped, normal subjects continue to show slow perceptual alternations (every few seconds), even though the stimuli are changing much more rapidly at each eye (2-3 Hz). At high rates of dichoptic alternation, a normal individual sees both patterns simultaneously instead of alternating.

Early diagnosis is important in relation to treatment and prevention of schizophrenia. However, this effort is hampered by the fact that psychiatric diagnosis is currently difficult and inaccurate. For example, between 50-70% of "first break" psychoses in young adults called "schizophrenia" are subsequently shown to be misdiagnosed.

There is a need for a simple objective method of diagnosing schizophrenia. It is apparent that this disorder is heterogeneous, so a subtype identification method could be useful in subsequent management as well as understanding of the condition.

SUMMARY OF THE INVENTION

The present inventors have surprisingly discovered a very high rate of perceptual alternation during binocular rivalry in schizophrenic and schizotypal individuals. The rates were so high that patients might have difficulty reporting their perceptual alternations accurately. The inventors discovered that a variant of binocular rivalry, dichoptic stimulus alternation (DSA), using rapid exchange of stimuli to the two eyes (Leopold and Logothetis, 1996) could be used. The inventors have found that DSA at frequencies much higher than a natural frequency of binocular rivalry can reveal underlying neural transitions that are faster than an observer's ability to respond due to beat frequency, or aliasing, effects between the rate of stimulus alternation and the endogenous neural rate. To the inventors' surprise, many patients maintained slow perceptual alternations even with very high speed DSA. This phenomenon may characterize a useful biological endophenotype or subtype for schizophrenia, as the presence of rivalry at rapid DSA was associated with particular anatomical features in patients, but not in controls. Binocular rivalry may provide a quantifiable measurement for diagnosis and understanding schizophrenia, schizophrenia subtypes and predisposition thereto.

The inventors have devised a method and apparatus for diagnosing schizophrenia, or a schizophrenic disorder subtype, or predisposition thereto. The present invention may have an advantage of significantly reduce misdiagnosis of schizophrenia. The diagnostic method may be useful in genetic linkage studies for identifying molecular defect(s) that may be associated with schizophrenia. New treatments could follow from the finding that a schizophrenic who can resolve high rates of dichoptic reversal also has more cognitive difficulties and reduced asymmetry of the temporal lobe as seen in MRI scans. Other aspects of the invention, including identifying a candidate therapeutic agent, will become apparent from the following description.

In a first aspect the invention broadly provides a method for diagnosing schizophrenia, schizophrenic disorder subtype, or predisposition thereto in a test subject, said method including the steps of:
(a) measuring an interhemispheric switch rate of the test subject; and
(b) comparing the measured switch rate with a corresponding reference switch rate to diagnose presence or absence of schizophrenia, schizophrenia disorder subtype or predisposition thereto.

Preferably, the interhemispheric switch rate is determined by measuring a rate of perceptual rivalry in the test subject.

The rate of perceptual rivalry may be determined by measuring a rate of reversal of perception of ambiguous optical stimuli.

Preferably, the rate of perceptual rivalry is determined by measuring a rate of binocular rivalry.

Alternatively, the interhemispheric switch rate may be determined by measuring a rate of the nasal cycle.

Preferably, the rate of perceptual rivalry is measured by:—
(i) displaying at least one image to the test subject, wherein the at least one image invokes perceptual alternation;
(ii) signalling respective incidences of perceptual alternation in the test subject during a predetermined period to provide a number of signals; and
(iii) dividing the number of signals by the predetermined period to provide the rate of perceptual rivalry.

Preferably, the method is characterised in that said signalling is effected by the test subject or by a suitable detection apparatus.

Preferably, the method further includes the step of processing each of the signals relating to interhemispheric alternation to convert these signals into digitised signals, and storing the digitised signals for subsequent use.

Suitably, presence of schizophrenia of a schizophrenic disorder subtype is diagnosed, or a predisposition thereto is suggested, when the interhemispheric switch rate of the subject is about equal to a corresponding reference switch rate range associated with schizophrenia or predisposition thereto.

In contrast, absence of schizophrenia or schizophrenia disorder subtype is determined, or predisposition thereto discounted, if the above criteria are not satisfied and/or when the interhemispheric switch rate of the subject is about equal to a corresponding reference switch rate range associated with a normal or control subject.

In a second aspect the invention provides a method for diagnosing schizophrenia, schizophrenic disorder subtype, or predisposition thereto in a test subject, said method including the steps of:
(1) measuring binocular rivalry rate in the subject; and
(2) comparing said measured binocular rivalry rate with a corresponding reference binocular rivalry rate to diagnose presence or absence of schizophrenia, schizophrenia disorder subtype, or predisposition thereto.

Preferably, diagnosis of schizophrenia or a predisposition thereto is indicated when the binocular rivalry rate is above 2.0 Hz.

More preferably, the binocular rivalry rate is above 2.5 Hz.

Diagnosis of a schizophrenic disorder subtype or predisposition thereto may be indicated when the binocular rivalry rate is in a range from 2.0 Hz to 10.0 Hz.

More preferably, the binocular rivalry rate is in a range from 2.5 Hz to 5.0 Hz.

Most preferably, the binocular rivalry rate is in a range from 3.3 Hz to 5.0 Hz.

In a third aspect the invention provides a method for diagnosing a schizophrenic disorder subtype or predisposition thereto in a test subject, said method including the steps of:
(A) measuring a dichoptic reversal rate whereby the subject is capable of perceiving that binocular rivalry persists; and
(B) comparing said measured dichoptic reversal rate with a corresponding reference dichoptic reversal rate to diagnose presence or absence of a schizophrenic disorder subtype or predisposition thereto.

Preferably, diagnosis of a schizophrenic disorder subtype or predisposition thereto is indicated when the subject can perceive binocular rivalry when the dichoptic reversal rate is greater than 4.0 Hz.

More preferably, the dichoptic reversal rate is greater than 7.5 Hz.

Even more preferably, the dichoptic reversal rate is greater than 15.0 Hz.

Most preferably, the dichoptic reversal rate is greater than 30.0 Hz.

Preferably, the stimulus for binocular rivalry is moving gratings.

Conversely, absence of a schizophrenic disorder subtype is determined, or a predisposition thereto discounted, when the subject cannot perceive binocular rivalry when the dichoptic reversal rate is above 4.0 Hz.

Preferably, the dichoptic reversal rate is above 7.5 Hz.

Even more preferably, the dichoptic reversal rate is above 15 Hz.

Preferably, the stimulus for binocular rivalry is moving gratings.

In fourth aspect the invention provides a method of treating a patient with schizophrenia or a schizophrenic disorder subtype including the steps of:—
(a) measuring an interhemispheric switch rate of the patient;
(b) comparing said measured interhemispheric switch rate with a range of reference interhemispheric switch rates associated with schizophrenia or schizophrenia disorder subtype; and
(c) administering to said patient a pharmaceutically-effective dosage of a drug for treating schizophrenia or a schizophrenic disorder subtype, when said measured interhemispheric switch rate is in said range.

Preferably, diagnosis of schizophrenia, schizophrenia disorder subtype, or a predisposition thereto is indicated when the measured interhemispheric switch rate above 2.0 Hz.

More preferably, the measured interhemispheric switch rate above 2.5 Hz.

Diagnosis of a schizophrenic disorder subtype or predisposition thereto may be indicated when the measured interhemispheric switch rate is in a range from 2.0 Hz to 10.0 Hz.

More preferably, the measured interhemispheric switch rate is in a range from 3.3 Hz to 2.5 Hz.

Most preferably, the measured interhemispheric switch rate is in a range from 3.3 Hz to 5.0 Hz.

In fifth aspect the invention provides a method of treating a patient with schizophrenia or schizophrenic disorder subtype including the steps of:—
(1) measuring a dichoptic reversal rate whereby the subject is capable of perceiving that binocular rivalry persists;
(2) comparing said measured dichoptic reversal rate with a corresponding reference dichoptic reversal rate to diagnose presence or absence of schizophrenia or schizophrenic disorder subtype; and (3) administering to said patient a pharmaceutically-effective dosage of a drug for treating schizophrenia or a schizophrenic disorder subtype, when said measured dichoptic reversal rate is in said range.

Preferably, the drug is administered to the patient when the patient can perceive binocular rivalry when the measured dichoptic reversal rate is above 4.0 Hz.

More preferably, the measured dichoptic reversal rate is above 15.0 Hz.

Even more preferably, the measured dichoptic reversal rate is above 30.0 Hz.

In a sixth aspect, the invention relates to an apparatus for diagnosing schizophrenia, schizophrenic disorder subtype, or predisposition thereto in a patient, said apparatus comprising:

(a) a monitor for monitoring interhemispheric switching in a test subject;

(b) processor for measuring an interhemispheric switch rate and for comparing said switch rate with a predetermined data set for providing diagnosis of presence or absence of schizophrenia, schizophrenic disorder subtype, or predisposition thereto; and (c) switching means for switching an image between eyes for producing a dichoptic reversal effect.

The monitor preferably is capable of presenting different viewing images separately to each eye and a recorder for recording when the subject perceives a change in the viewed image.

Preferably the different viewing images comprise a moving horizontal grating presented to one eye and a moving vertical grating presented to another eye. Alternatively, the different viewing images may be a stationary horizontal grating presented to one eye and a stationary vertical grating presented to another eye.

In one embodiment, the monitor incorporates a liquid crystal shutter before each eye, wherein the shutter may obstruct viewing of an image by respective right and left eye.

In another embodiment, an image is presented to each respective eye via a 3D head mounted display.

The recorder for recording perceived change may be a subjective device in the form of an indicator activated by the test subject when a change is perceived.

Preferably, the recorder is an objective device that records eye movements as an indicator of which image is being perceived. Alternatively, steady state visual evoked potentials may be measured to provide an objective indication of the perceptual alternation.

The processor suitably includes a timer and is capable of receiving signals from the recorder indicative of perceptual change.

The apparatus may also include a changer for inducing a change in ratio of total time spent perceiving left eye's presented image versus right eye's presented image.

In a seventh aspect, the invention relates to a method for diagnosing schizophrenia, schizophrenia disorder subtype, or predisposition thereto including the step of using the apparatus described in the sixth aspect to determine interhemispheric switching rate in a patient.

In an eighth aspect the invention provides a process for identifying one or more genetic markers associated with schizophrenia, schizophrenic disorder subtype or predisposition thereto as herein described, said process including the steps of:

(a) testing respective members of one or more pedigrees affected by schizophrenia, or schizophrenic disorder subtype, using the method of any one of the above aspects of the invention;

(b) identifying members having schizophrenia, schizophrenic disorder subtype or predisposition thereto; and (c) conducting genetic linkage analysis on the identified members to identify the one ore more genetic marker associated with schizophrenia, or schizophrenic disorder subtype.

In a ninth aspect the invention provides a genetic marker identified according to the eighth aspect.

In a tenth aspect the invention provides a method for diagnosing schizophrenia, schizophrenic subtype or predisposition thereto in a test subject said method including the steps of:

(i') displaying at least one image to the test subject, wherein the at least one image invokes perceptual alternation;

(ii') scanning the brain of the test subject during perceptual alternation;

(iii') detecting an anatomical structure in the brain of the test subject; and (iv') comparing the detected anatomical structure with a corresponding reference anatomical structure to diagnose presence or absence of schizophrenia or schizophrenic subtype.

Preferably, scanning is by functional MRI, positron emission tomography, MEG or multi-electrode VEP.

Preferably, perceptual alternation is invoked by dichoptic reversal stimuli.

BRIEF DESCRIPTION OF THE DRAWINGS AND TABLES

In order that the invention may be readily understood and put into practical effect, preferred embodiments of the invention will be described with reference to the attached drawings.

FIG. 1 shows one embodiment of a diagnostic apparatus useful for diagnosing schizophrenia as herein described. Shown is a psychophysical set-up used to examine binocular rivalry. To avoid problems with binocular fixation and alignment, the rivalrous stimuli are presented at the same location. By alternating rapidly between the rivalrous stimuli in phase with liquid crystal shutters, each eye's view can be restricted to the stimulus intended for it. The subject reports the perceived stimulus by depressing one of three keys for horizontal, vertical, or mixed/indeterminate percepts.

Figure 4:
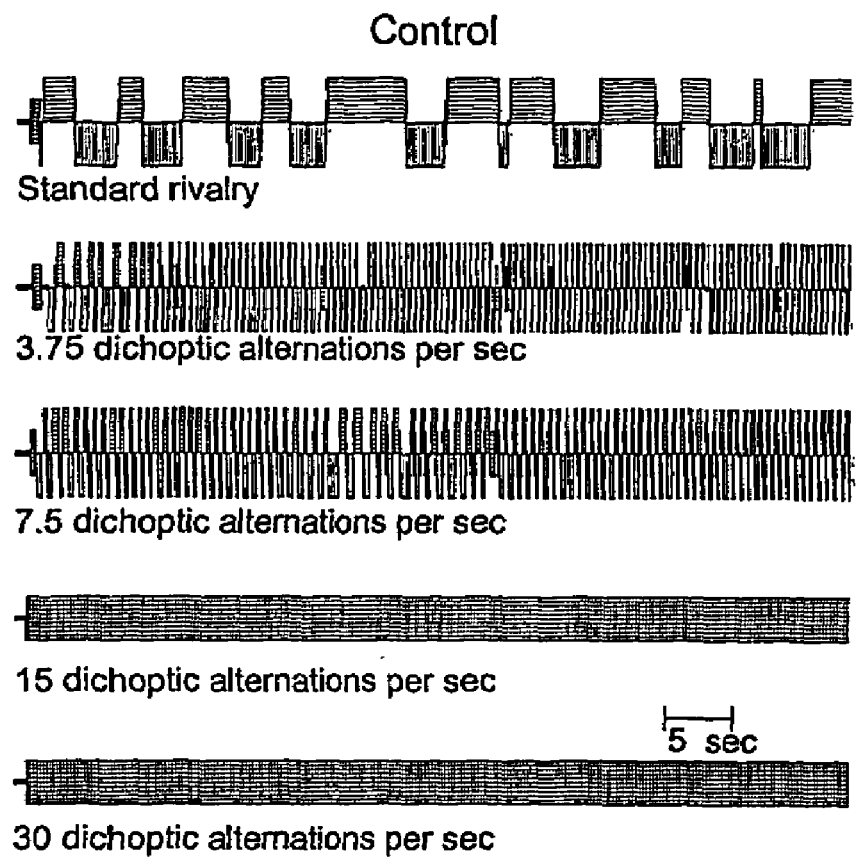

FIG. 4: Binocular rivalry at increasing rates of Dichoptic Stimulus Alternation for a Control. When traditional rivalrous stimulation was maintained with the same constant pattern of stimulation on each retina (horizontal grating to the right eye, vertical grating to the left eye), note that the individual's perception switches among three percepts: (a) horizontal dominance (shown as horizontal lines in the time blocks above the line); (b) vertical dominance (indicated by vertical lines in the time blocks below the line); and (c) a blended percept, that is relatively infrequent in this individual, where both horizontal and vertical percepts co-exist as a "plaid" or "crosshatch" (shown in time blocks straddling the line). When the rivalrous stimuli alternate between eyes at the slower rates (3.75 and 7.5 Hz), this control individual reports rapidly alternating horizontal/vertical dominance periods as though tracking the rapidly alternating switches of orientation. There is no perceptual alternation reported at reversal rates of 15 or 30 Hz, rather the blended percept was always reported. All control individuals reported the blended percept at least 90% of the time with 30 Hz dichoptic stimulus alternations.

Figure 5:
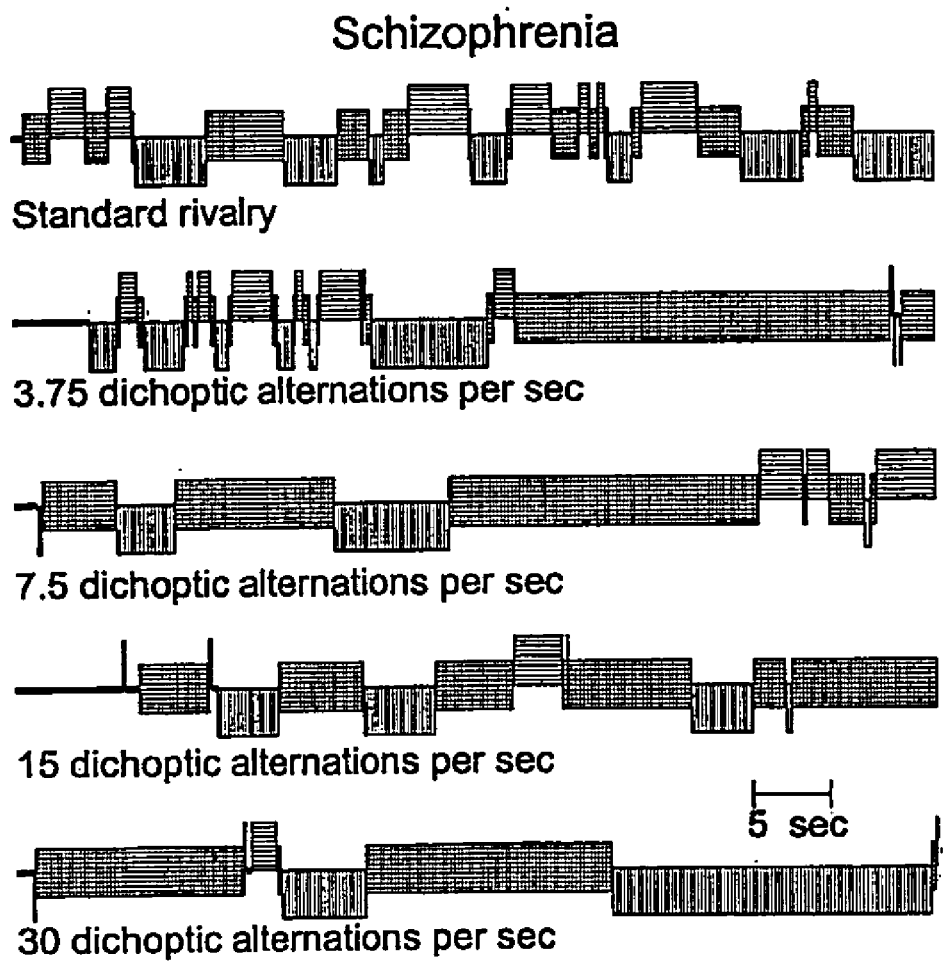

FIG. 5: Binocular rivalry at increasing rates of dichoptic stimulus alternation for a schizophrenic patient. Same conventions as FIG. 4. Note that this subject continues to experience slow alterations between the horizontal and vertical percepts even when the stimuli at each eye are being exchanged (DSA) at rates as high as 30 Hz. During traditional rivalrous stimulation perception switches among horizontal dominance, vertical dominance, and the blended percept as seen for the control observer in FIG. 4. When the rivalrous stimuli alternated between the eyes, however, periods of horizontal or vertical dominance lasting for seconds are interspersed with periods of the blended percept. Perceptual alternation was reported with dichoptic stimulus alternation rates up to 30 Hz by 16 of 24 patients with schizophrenia. This patter of response may also typical for a subgroup B schizophrenic.

Figure 6:
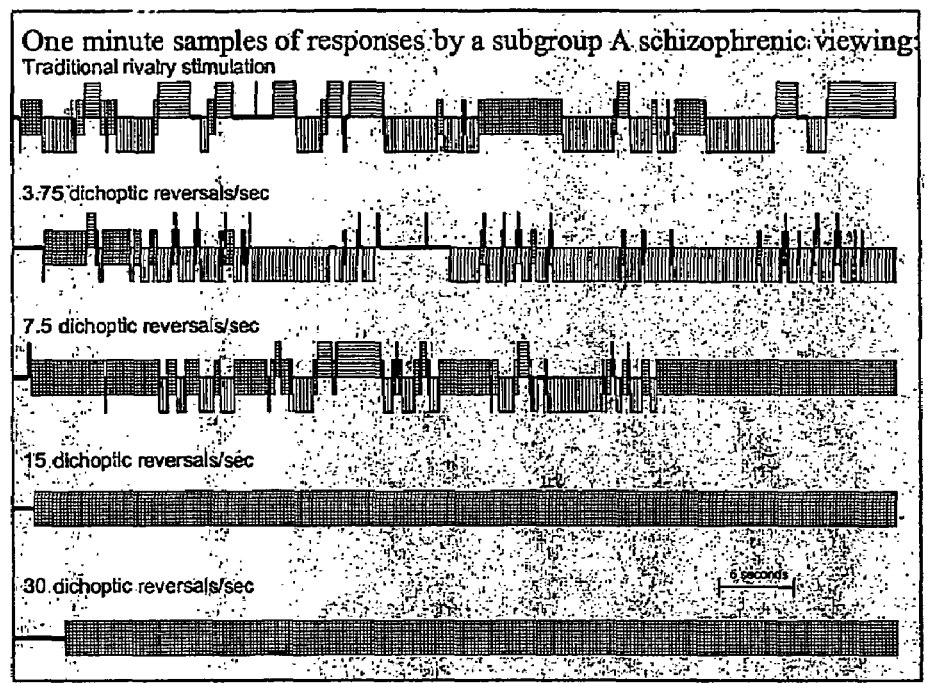

FIG. 6 shows a tracing for traditional rivalry and different dichoptic reversal rates for subgroup A schizophrenics. Same conventions as FIGS. 4 and 5.

Figure 7:
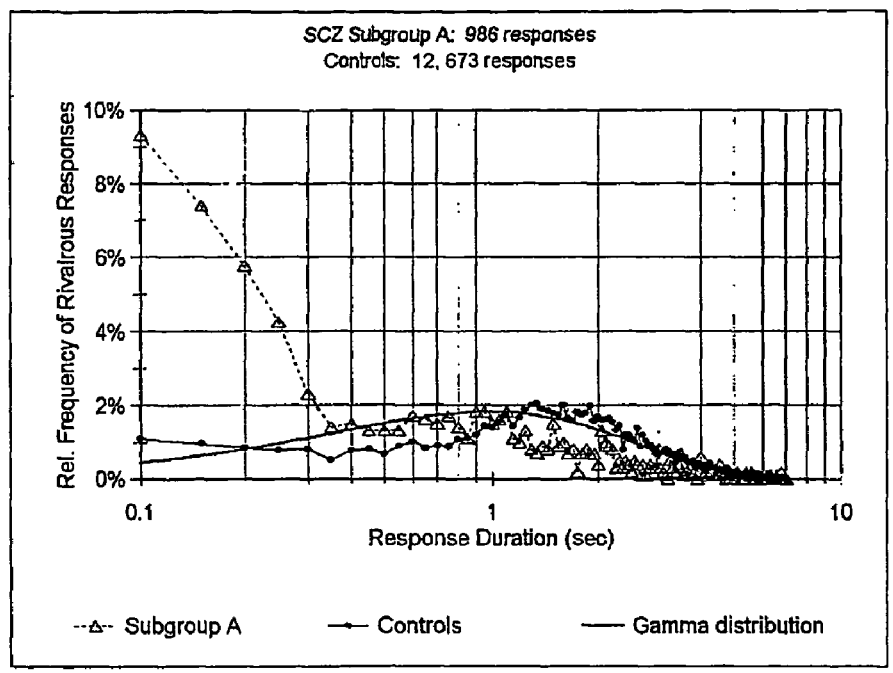
Figure 7:
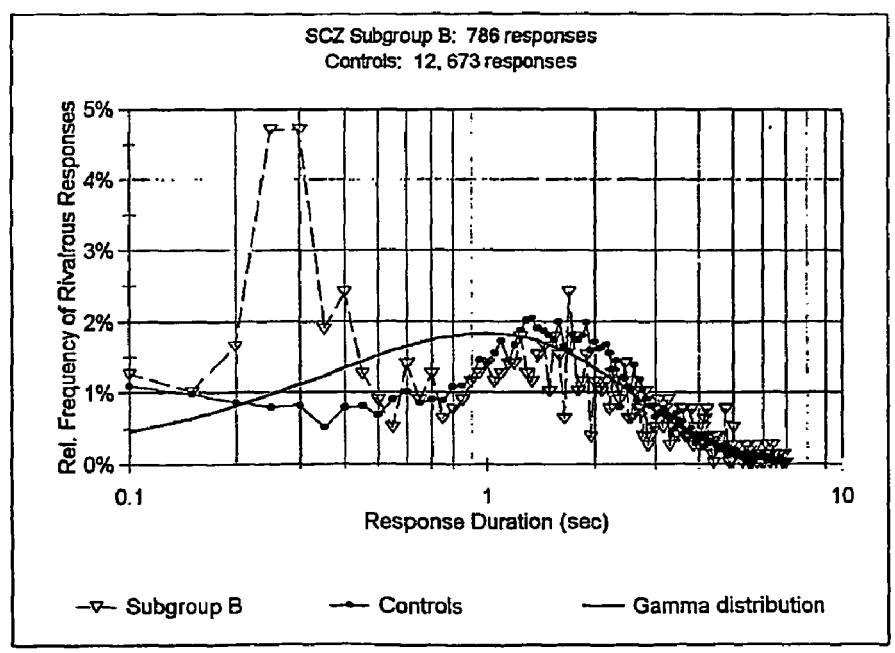

FIG. 7 shows two graphs illustrating fast binocular rivalry in schizophrenic subgroup A (FIG. 7A) and subgroup B (FIG. 7B).

Figure 8:
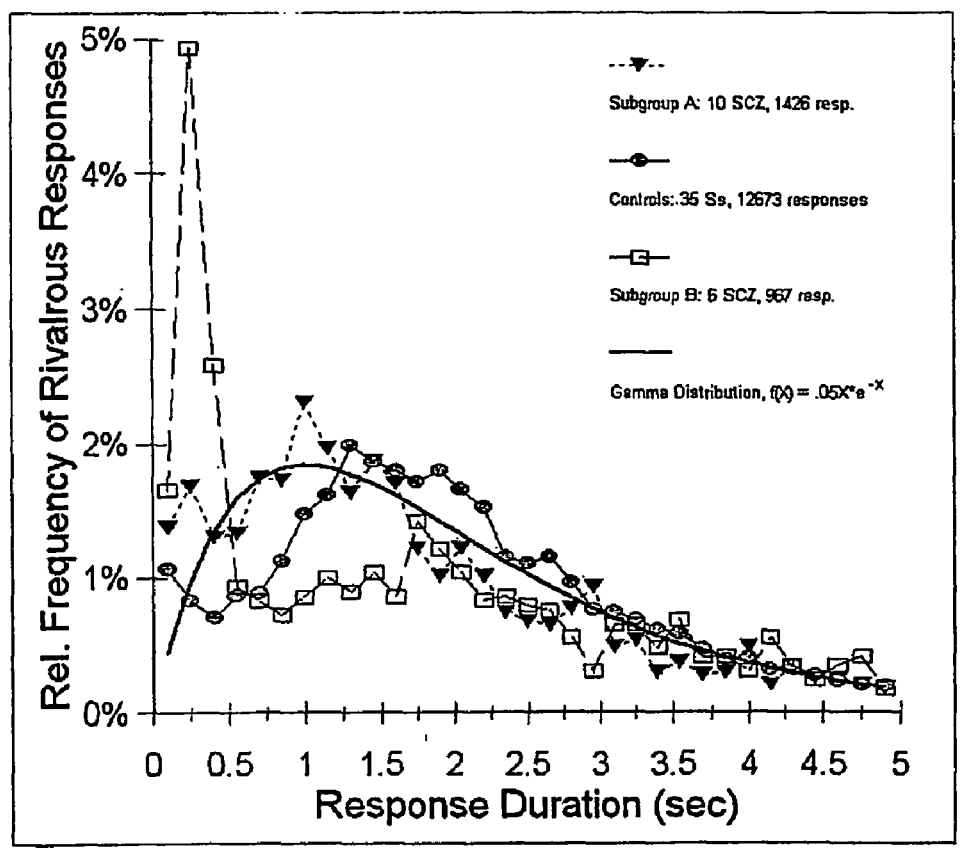

FIG. 8 shows relative frequency of rivalrous response results for traditional rivalry for schizophrenic subgroups A and B, with controls.

Figure 9:
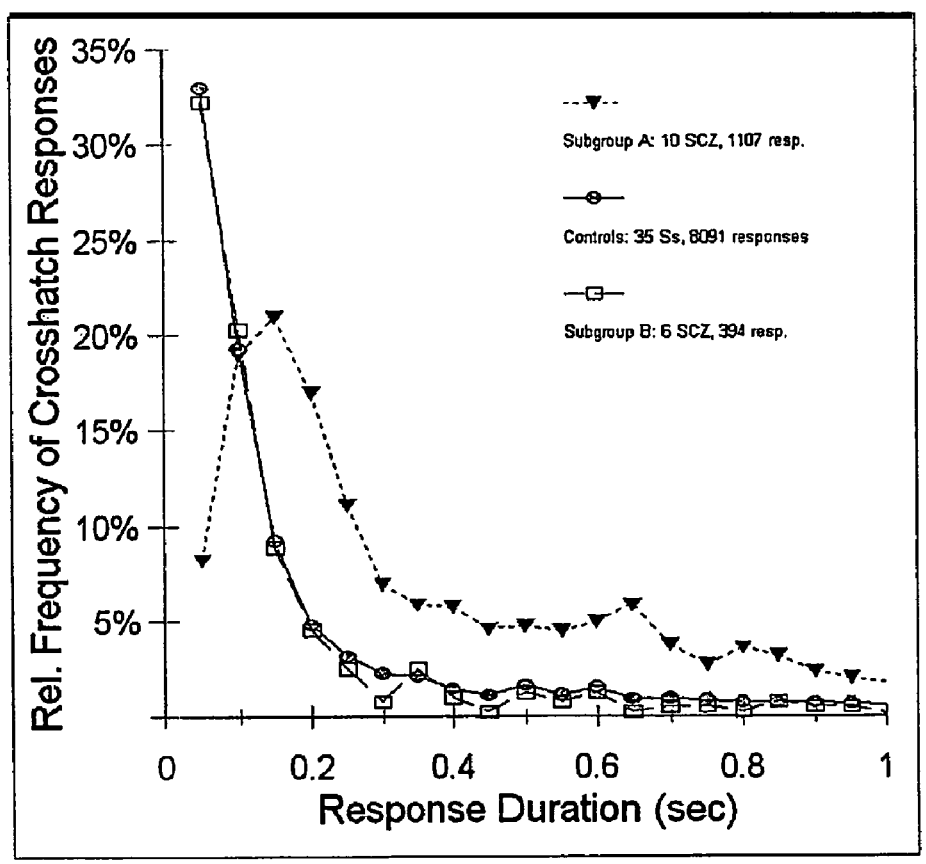

FIG. 9 shows relative frequency of crosshatch response results for traditional rivalry for schizophrenic subgroups A and B, with controls.

Figure 10:
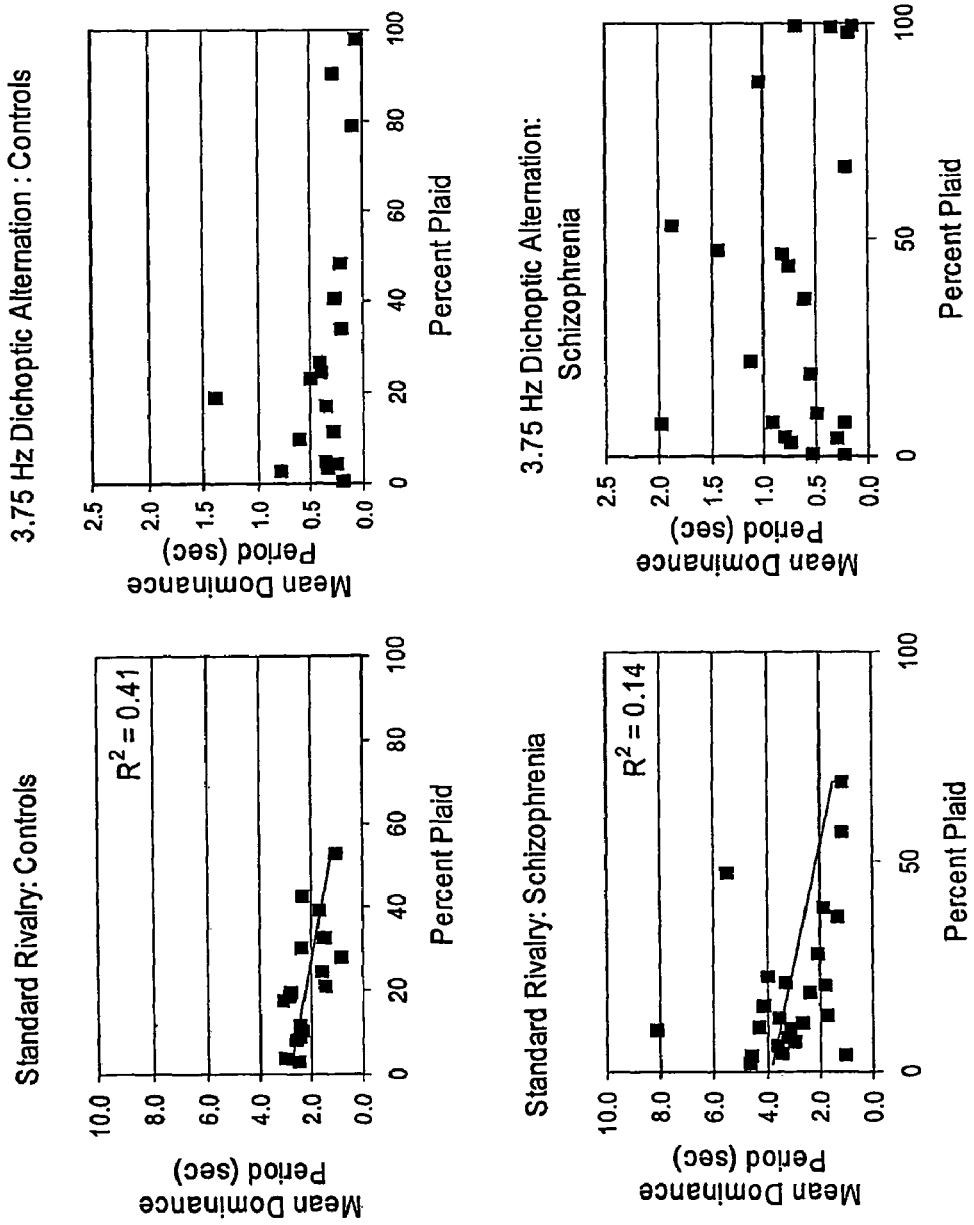

FIG. 10. Quantitative measures of binocular rivalry in controls and schizophrenic patients. Mean dominance period (duration of a stable percept of one alternative stimulus between switches) plotted as a function of the percent time spent perceiving "plaid" where both alternatives, horizontal and vertical gratings, were present simultaneously. Under standard rivalry conditions where there was no dichoptic stimulus alternation (0 Hz DSA), both controls and schizophrenics show a tendency for individuals experiencing more "plaid" to have shorter dominance periods (faster alternation rates). Patients show longer periods of stable rivalry under both conditions. There is a negative relationship between stability of rivalry and time in plaid for controls under standard rivalry conditions [$F(1,16)=11.11$, $p<0.005$]. The relationship is weaker in schizophrenia [$F(1,22)=3.6$, $p=0.07$]. There is no relationship between these two variables at 3.75 Hz DSA or higher rates (not shown). At a slow rate of dichoptic stimulus alternation (3.75 Hz) (note the different scale), most controls show short dominance periods (high alternation rates) in keeping with the fast switching of stimuli, but a number of schizophrenics show long dominance periods. This divergence between the two groups becomes even more obvious at higher DSA rates (see FIG. 11).

Figure 11:
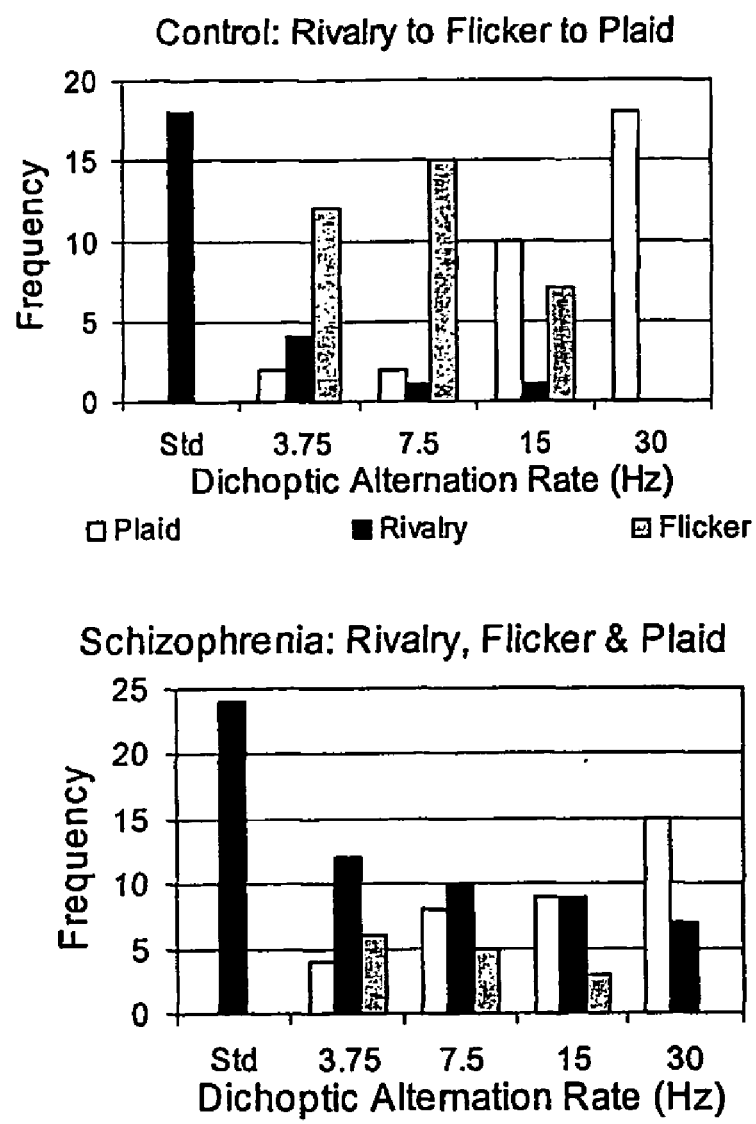

FIG. 11. The number of individuals reporting stable rivalry (MDP>0.5 sec control, % plaid<90), high frequency alternation (MDP<0.5 sec, % plaid<90) or >90% plaid in the two groups. All individuals, regardless of diagnosis report stable rivalry under standard conditions. Most controls report flicker under low rates of DSA and plaid under high rates of DSA. No control individuals report stable rivalry above 7.5 Hz. Patients report rivalry at all DSA, while the number reporting plaid increases and the number reporting flicker decreases. The dependence of these phenomena on DSA rate provides some confidence that S are accurately reporting their perceptions, not randomly pressing the mouse buttons. The underlying distributions were significantly different at all DSA (see Table 2).

Figure 12:
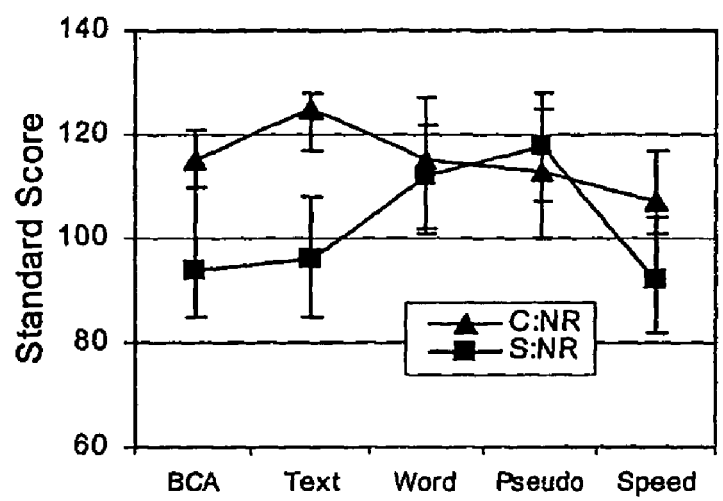
Figure 12:
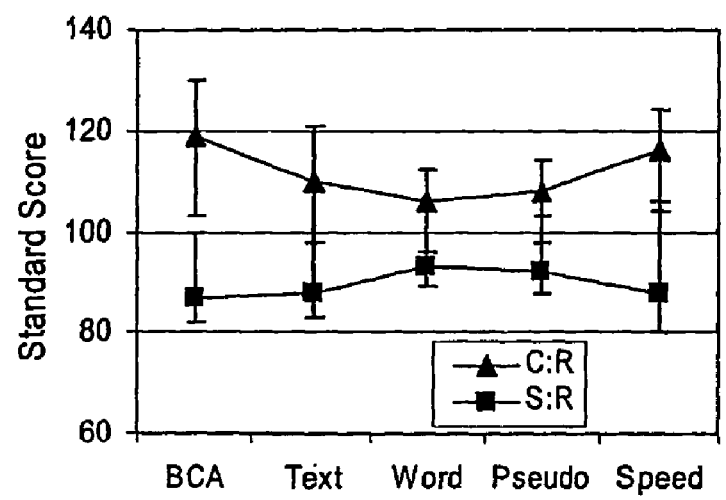

FIG. 12. Cognitive and reading skills as a function of diagnosis and rivalry. Patients who show stable rivalry for at least one rapid DSA rate were more likely to have consistently low cognitive function and reading skills. Patients who did not show stable rivalry had superior phonological decoding and single word reading skills, abilities that are supposedly resistant to cognitive decline in schizophrenia.

Figure 13:
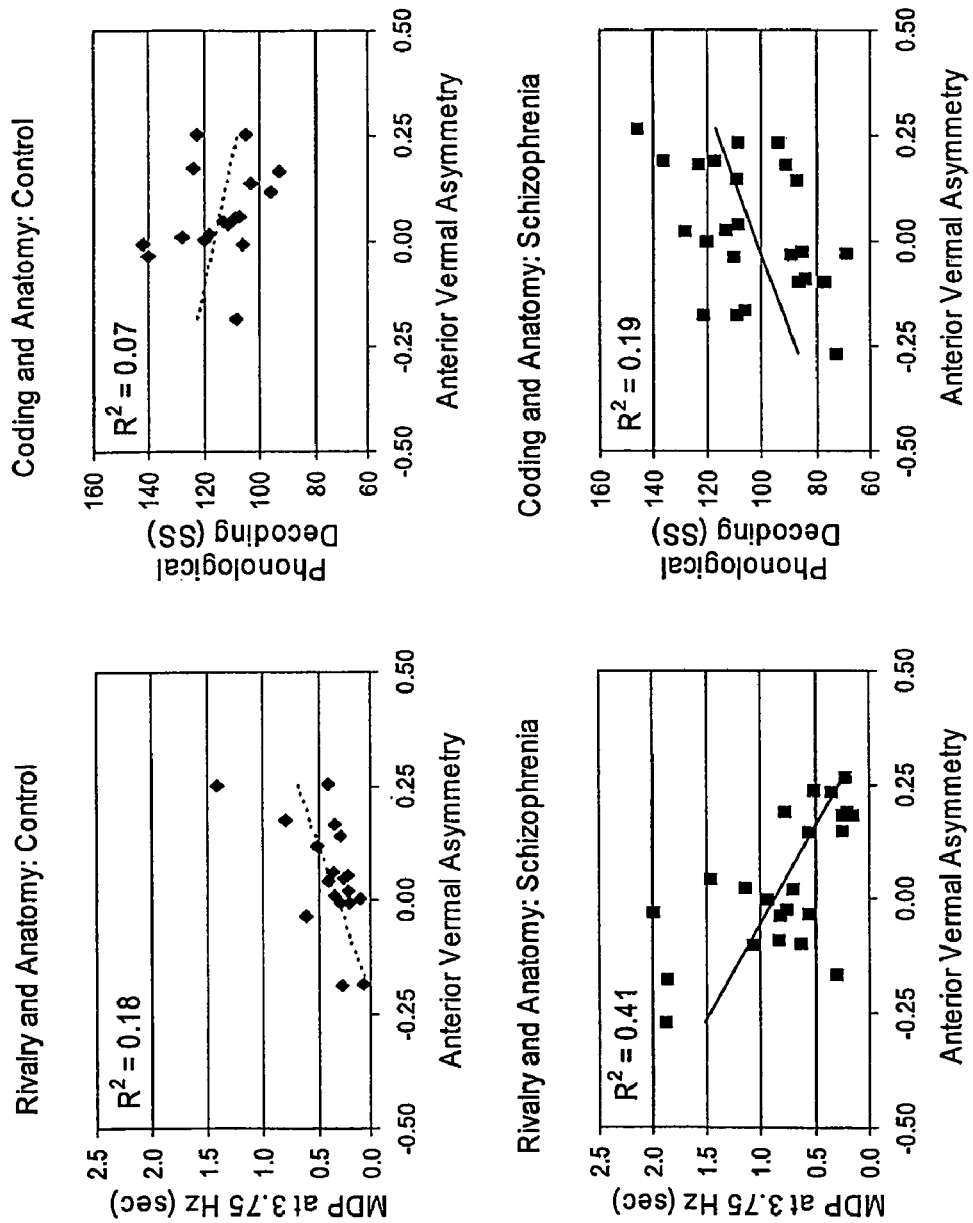

FIG. 13. The relation between rivalry under DSA (MDP at 3.75 Hz), cerebellar asymmetry and pseudoword reading skill (a measure of phonological decoding). Patients with schizophrenia who have rightward cerebellar asymmetry are much more likely to have long MDP at 3.75 Hz and poor phonological decoding. In controls there is no relation between MDP, anatomy and phonological decoding.

Figure 14:
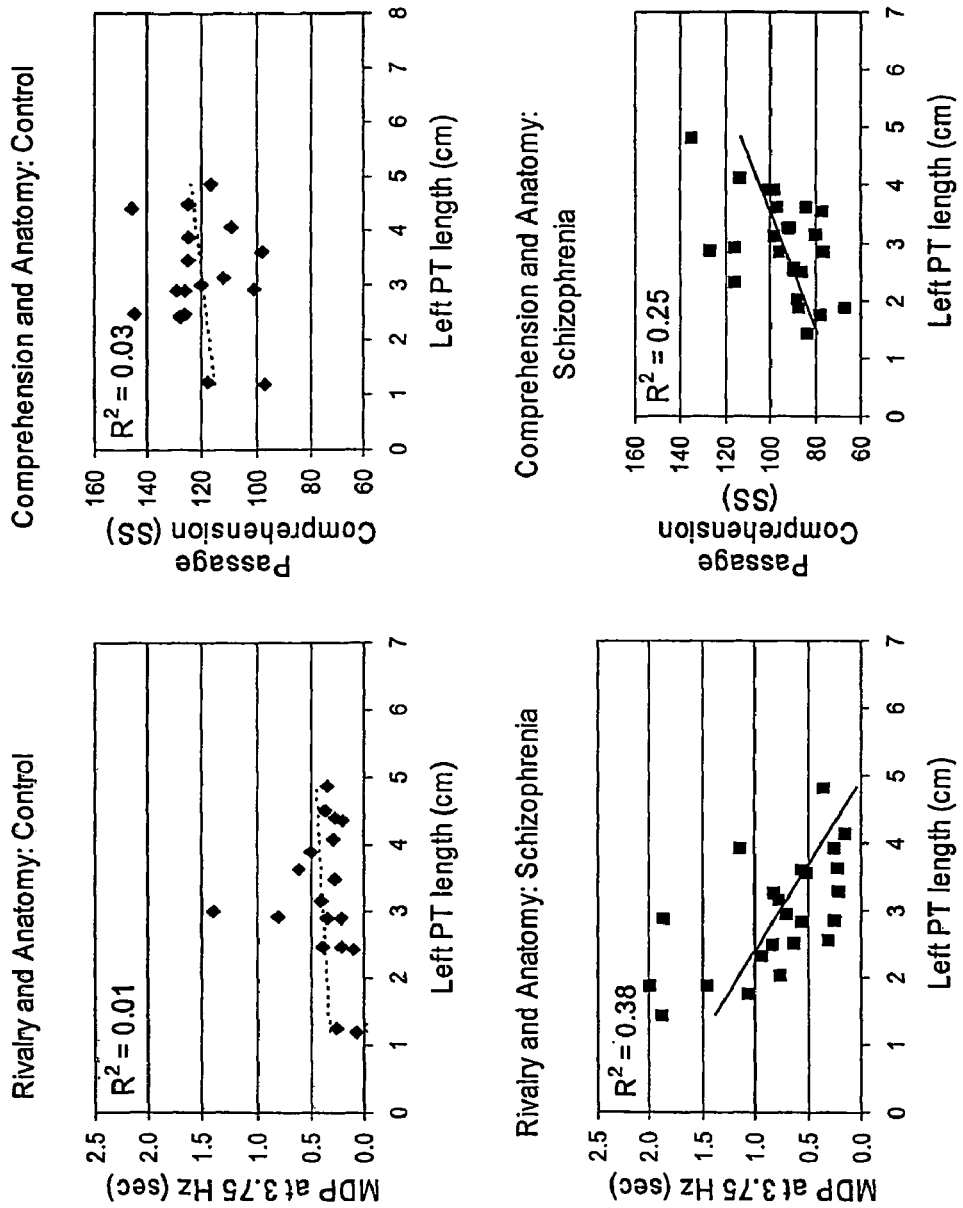

FIG. 14. The relation between MDP at 3.75 Hz, planar anatomy and reading skill. Patients with schizophrenia who have short left PT are much more likely to have long MDP at 3.75 Hz and poor text comprehension. This relation between planar length and comprehension has been seen in other studies. In controls there is no relation between MDP and PT length or reading comprehension, perhaps due to a restriction of range. Almost all controls have short MDP and excellent comprehension.

Figure 15:
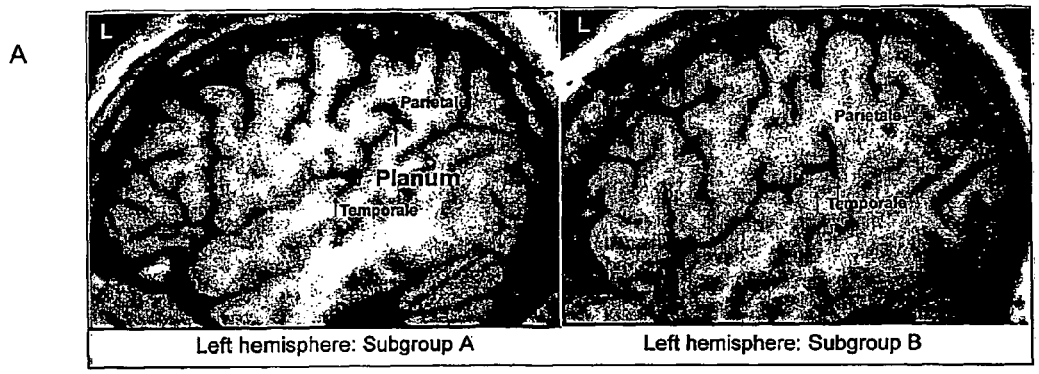

FIG. 15 shows a scanned image of a left hemisphere brain slice from respective individuals from schizophrenic subgroups A and B.

Figure 16:
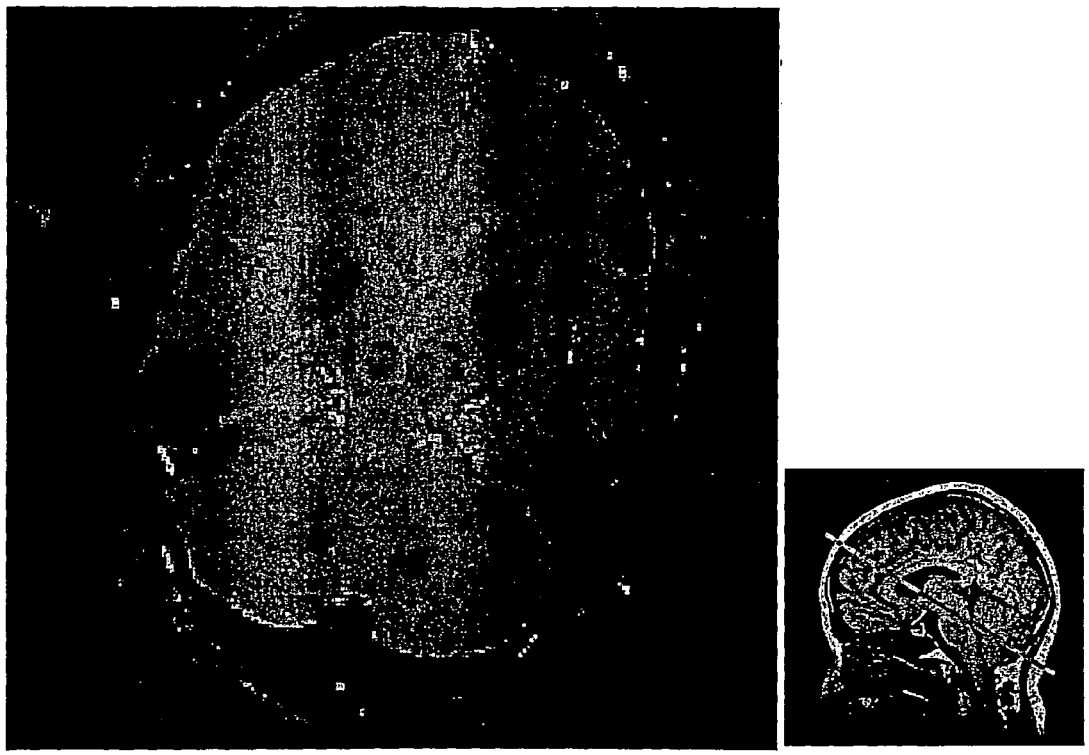

FIG. 16 shows an example of a high resolution fMRI single slice.

Table 1: Demographic information on two groups. SES: socioeconomic status; PANSS: Positive and Negative Symptom Scale (Kay et al., 1992).

Table 2: Median and interquartile range for the mean dominance period as a function or dichoptic stimulus alternation rate (DSA) in the schizophrenic patient and matched control groups. The significance of is the differences was tested with the Kruskal-Wallis one way analysis of variance by ranks (Siegel, 1956).

Table 3: Performance of the two groups during the training movie.

Table 4: The number of times that individuals in each group reported rivalry (MDP greater than 0.5 sec and % plaid<90) at rapid DSA rates.

Table 5: Characteristics of schizophrenia subgroups A and B.

DETAILED DESCRIPTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "schizophrenia" is meant a mental disorder with a tendency towards chronicity which impairs functioning and which is characterised by psychotic symptoms involving disturbances of thinking, feeling and behaviour (The American Psychiatric Association's Diagnostic and Statistical Manual, 3rd edition). The condition is probably manifested by heterogeneous conditions or subtypes.

By "ambiguous optical stimuli" is meant those stimuli able to elicit different perceptions which alternate during continued observations of the same stimulus. Suitable ambiguous stimuli of this type include ambiguous figures such as the Necker cube and Schröder staircase.

The term "binocular rivalry" refers to the alternating perceptual states that arise when viewing different images, presented separately to each eye, in the same retinal location. In this regard, it is well known that when corresponding regions of the two eyes are stimulated by sufficiently different patterns, the stimuli rival in terms of conscious perception, rather than fuse into a composite pattern. Accordingly, a perceptual alternation or switch between these nonfusible dichoptic stimuli results. Binocular rivalry rate (Hz) is converted to response duration or rivalry period (seconds) by calculating the inverse.

By "dichoptic" is meant different stimuli to each eye. Dichoptic stimulation is the basis of a procedure for producing binocular rivalry, but usually the different stimuli are presented constantly to each eye.

By "dichoptic reversal" is also meant "dichoptic stimulus alternation (DSA)" that means stimuli are always different in each eye (dichoptic) and that they are swapped therebetween. For example, if a right eye of a subject is viewing horizontal lines and a left eye is viewing vertical lines in the first second, in the second the left eye will be viewing horizontal and the right eye viewing vertical. Rate of swapping can be varied, for example from 0 to 30 Hz.

By "interhemispheric switch rate" is meant the rate of interhemispheric alternation in one or more regions of the brain inclusive of temporo-parietal cortex, hypothalamus, prefrontal, and limbic regions of the brain. Preferably, the interhemispheric switch rate relates to the rate of interhemispheric alternation of the temporo-parietal cortex.

The term "genetic marker" includes within its scope a region of a chromosome, locus, allele or fragment thereof that is associated with a particular phenotype.

Binocular Rivalry

The present invention relates to a test subject viewing a drifting grating of horizontal high-contrast bars which is presented to a right eye of the subject while a similar drifting vertical grating is presented to a left eye of the subject. Under these conditions a base line data set is collected as the subject reports the perceptual alternations between horizontal and vertical. After collecting the baseline data on rates of alternation, dichoptic alternation is begun. The patterns are now switched between eyes in one embodiment by changing the phase of liquid crystal shutters of a pair of glasses in reference to a vertical synch signal from the display. Thus, at one point the right eye is exposed to horizontal stripes while the left eye is exposed to vertical stripes; in the next block of time the eyes are reversed and the right sees vertical while the left eye sees horizontal. As first described by (Logothetis, Leopold et al. 1996), incorporated herein by reference, the reversals do not disrupt rivalry if they occur below a certain rate. The reversals may occur at 3 Hz yet the subject will still experience the usual form of rivalry every few seconds, much slower than the dichoptic reversal rate. If the dichoptic reversal rate is increased above 4 Hz, normal subjects no longer rival, but instead see a blend of both stimuli, such as a "grid, crosshatch or plaid". Remarkably, some schizophrenics continue to experience normal rivalry, changing their perception from horizontal to vertical and back, every few seconds, even though the dichoptic reversal rate as high as 30 Hz. Example 2 refers to use of a head mounted display for producing dichoptic alternation.

The present invention relates to a multi-faceted approach to schizophrenia using cognitive testing, psychophysical investigation of temporal aspects of perception using binocular rivalry (including dichoptic reversal), and functional and anatomical brain imaging. The inventors surprising discovered that a striking feature of perceptual processing in schizophrenics that might act to link all these approaches: viz:—a schizophrenic has unusually fast binocular rivalry compared to a normal subject. More significantly, a sub-group of schizophrenics show a phenomenon that involves machine-like resolution (even at a dichoptic reversal rate of 30 Hz) of a rapidly-alternating pattern in binocular rivalry [(White K., et al. 2001)]. This same sub-group appears to have significant cognitive impairment and reduced asymmetry of the planum temporale and thus raises the possibility for recognising a new endophenotype.

Additional observations linked to the rivalry findings are anomalous planar morphology on magnetic resonance imaging (MRI) scans and poor reading and language skills. This new classification method may be useful for predicting response to medication, symptom severity and other clinical features. As well as improving diagnosis of schizophrenia, it is possible that abnormal rivalry could serve as an early neurobehavioral marker for persons at risk.

Readily quantifiable features of binocular rivalry can be used to gain insight into higher order dysfunctions of mood and cognition such as schizophrenia and bipolar disorder. For example, striking perceptual shifts of binocular rivalry, which occur despite a constant visual input, can be linked to attentional-like shifts between hemispheres so that the relative time spent in each percept directly yields the relative times spent in each cerebral hemisphere (Miller, Liu et al. 2000), incorporated herein by reference.

Manipulations of one hemisphere may produce changes in rivalry that reflect the hemisphere being stimulated (caloric vestibular stimulation) or disrupted (transcranial magnetic stimulation; TMS). For example, in the commonly-used paradigm where the right eye views a horizontal grating and the left eye views a vertical grating, activation of the left hemisphere increases the proportion of time spent by most subjects seeing horizontal. In contrast, left hemisphere TMS disrupts the perception of horizontal if delivered during the phase when horizontal is perceived. In initial studies it was difficult to show exactly symmetrical effects of right hemisphere-specific manipulations, but recent work with greater temporal precision based on pre-programmed TMS pulses has shown similar effects in the right hemisphere at the opposite phase (Funk 2001), incorporated herein by reference. This phase-specific, hemisphere-specific pattern of disruption strongly supports the interpretation that rivalry is mediated by a switch of an attentional-like process between hemispheres (Miller, Liu et al, 2000; Funk 2001). When combined with growing evidence that mood valence is hemispheric, these findings have the implication that rivalry can provide a quantifiable measure that can be used to follow a patient's response to treatment, for example.

In addition to revealing the predominance of hemispheric activity, binocular rivalry also reveals precise details of neural timing. The rate of switching between rivalrous percepts is highly reproducible in individuals measured years apart [r=0.85, (Pettigrew and Miller 1998)], incorporated herein by reference, and shows a similarly high concordance in monozygotic twins, despite its wide interindividual variation (period=0.5-20 sec; N=300). Slow rates are found in bipolar disorder, with virtually all subjects having a rivalry period greater than 4 seconds also having Bipolar I disorder. In contrast, schizophrenics show short rivalry periods and have a number of other striking differences from both normal and bipolar subjects.

FIG. 7 shows fast binocular rivalry in schizophrenia. Note that both schizophrenic subgroups have more intervals between rivalrous percepts in near 0.2 seconds (5.0 Hz), and fewer intervals in the 1-2 second range compared with normal controls. These effects were also seen independent of medication. Sub-group B had rivalry that survived dichoptic reversals as fast as 30 Hz.

The surprising finding that schizophrenics continue to experience rivalrous alternations despite very high dichoptic reversal rates up 30 Hz may has several implications. First, this finding bears upon a heated question of a mechanism of rivalry and a neural locus of its components such as the oscillator and a putative switch between hemispheres. If a schizophrenic is so different from a normal individual in rivalry, investigation of this quantifiable aspect of neural timing might provide a mutual illumination of the currently-disputed mechanisms of both schizophrenia and rivalry. This viewpoint is supported by the observations that all schizophrenics so far studied seem to be characterised by faster timing in rivalry, with subgroup B and group SR showing an extraordinary high speed ability to resolve dichoptic reversal.

Investigation of rivalry in schizophrenia with both psychophysical methods and scanning techniques may illuminate some of the present unknowns, such as a basis for altered neural timing as measured in rivalry of schizophrenia. Since there is evidence that the interhemispheric switching is very slow in frontal cortex compared with more posterior visual regions (Shannahoff-Khalsa and Yates 2000), incorporated herein by reference, a testable hypothesis to account for this result involves a greater involvement of a machine-like, stimulus-locked posterior cortical regions in the schizophrenic rivalry switch, compared with a normal individual, where the involvement of more frontal regions may be greater. Testing this idea using fMRI during rivalry could help to answer the question as well as throwing light on the nature of the elusive switch itself. This hypothesis does not conflict with recent data from schizophrenic patients showing reduced frontal measures of information content and coherence with other cortical regions compared to normal individuals, despite equality of measured frontal activity in both groups (Tononi and Edelman 2000), incorporated herein by reference.

Quantifiable measures provided by binocular rivalry may be linked to clinical parameters such as reading and cognitive measures, symptomatology, course of illness, treatment resistance, side effects from, and response to, medication. Since thousands of data points can be collected in a short time from a procedure with potentially high patient acceptance. It is possible that binocular rivalry, once linked to other clinical parameters by the investigations proposed herein, could provide a useful adjunct to more protracted assessments with less patient acceptability.

Diagnosis of Schizophrenia Using Interhemispheric Switch Rates

The inventors have devised a method for diagnosing schizophrenia, or a schizophrenic disorder subtype, or predisposition thereto based on the surprising finding of a high rate of perceptual alternation during binocular rivalry in schizophrenia. The method includes the steps of determining an interhemispheric switch rate of a test subject, and comparing the switch rate with a corresponding reference switch rate to diagnose presence or absence of the schizophrenic disorder subtype or predisposition thereto. In this regard, the invention broadly encompasses diagnosing schizophrenia, a schizophrenic disorder subtype or predisposition thereto as herein described when the interhemispheric switch rate is aberrant relative to a normal range of interhemispheric switch rates.

The interhemispheric switch rate of the subject may be determined by any suitable technique and, in this regard, techniques that indirectly measure a particular interhemispheric switch rate are also contemplated by the invention. For example, an interhemispheric switch rate relating to the temporo-parietal cortex may be determined by measuring the rate of perceptual rivalry (or perceptual alternation) in the subject. Alternatively, an interhemispheric switch rate relating to hypothalamic activity may be determined by measuring rate of alternating sympathetic and parasympathetic activity in the nasal turbinates, also known as the nasal cycle (Shannahoff-Khalsa, 1993, *Intern. J. Neuroscience* 70:285-298, which is incorporated herein by reference).

Preferably, the step of determining interhemispheric switch rate is characterised by subjecting a test subject to a stimulus that invokes interhemispheric alternation therein. Any suitable stimulus having such characteristics is contemplated by the invention and in this regard, the stimulus may comprise images that are sufficiently different that rivalry is induced rather than fusion; i.e. perceptual rivalry is induced.

The rate of perceptual rivalry may be determined by measuring the rate of reversal of perspective for ambiguous optical stimuli, for example by viewing the Necker cube or Schroder staircase. Exemplary methods which may be used to measure the rate of reversal of perspective include, but are not limited to, those disclosed in George (1935, *J. Gen. Psychol.* 39-59), Washburn and Manning (1933, In *Studies from the psychological laboratory of Vassar College* 632-633), Washburn et al (1933, ibid 633-636), Washburn et al (1933, ibid 636-637), and Borsellino et al (1972, 10.Bd., *Heft* 3:139-144), which are incorporated herein by reference.

Preferably, the rate of perceptual rivalry is determined by measuring the rate of binocular rivalry. Examples of binocular rivalry techniques include, but are not limited to, those disclosed in Howard and Rogers (1995, "Binocular fusion and rivalry", In *Binocular Fusion and Stereopsis*, eds Mackintosh et al., Oxford University Press), Logothetis et al (1996, *Nature* 380:621-624), Kovacs et al (1996, *Proc. Natl. Acad. Sci. USA* 93:15508-15511), Sheinberg and Logothetis (1997, *Proc. Natl. Acad. Sci. USA* 94:3408-3413), and Andrews and Purves (1997, *Proc. Natl. Acad. Sci. USA* 94:9905-9908), which are incorporated herein by reference.

Suitably, the rate of perceptual rivalry is measured by displaying an image to the test subject which image invokes perceptual alternation, signalling respective incidences of perceptual alternation in the test subject during a predetermined period to provide a number of signals and dividing the number of signals by the predetermined period to provide the rate of perceptual rivalry.

Preferably, the method is characterised in that said signalling is effected by the test subject or by a suitable detection means. In the case of a subject effecting the signalling, the subject preferably signals a perceptual alternation or switch. In this context, the subject may signal visually, audibly, or by touch wherein the signal is registrable by a suitable sensor. For example, the subject may depress a button that is suitably operably connected to a signal registration means that registers the signal.

Alternatively, a perceptual alternation may be signalled by a suitable detection means. For example, the detection means may be adapted to measure visually evoked potentials (VEP). In this regard, reference may be made for example, to Brown and Norcia (1997, *Visions Res.* 37:2401-2408, which is incorporated herein by reference) which teach a real-time, steady-state VEP based on labelling each eye's image with a slightly different temporal frequency so that the record generated by each can be recovered by an electroencephalogram (EEG) by spectrum analysis. In this way, it is possible to track the "waxing" and "waning" of the VEP amplitudes for each eye's image simultaneously during spontaneous rivalry, permitting an analysis of the relative dominance of each eye's image in real-time and to determine alternation rate.

Alternatively, the detection means may be adapted to monitor eye movement. For example, Blackwood et al (1996, *Br. J. Psych.* 168:85-92, incorporated herein by reference) teach a smooth-pursuit eye tracking procedure in which a subject visually tracks an image and an electrooculograph is recorded in the horizontal plane via electrodes attached adjacent to the outer canthus of each eye. Reference also may be made to Sweeney et al (1998, *Biol. Psychiatry* 43:584-594, incorporated herein by reference) who disclose the use of infrared recordings to monitor eye movements. Such procedures that monitor eye movements have particular utility in binocular rivalry methods that rely on moving dichoptic stimuli, such as moving vertical and horizontal gratings.

Alternatively, the interhemispheric switch rate may relate to the rate of interhemispheric alternation of hypothalamic activity as mentioned above. Such rate may be determined by measuring the rate of alternating sympathetic and parasympathetic activity in the nasal turbinates, otherwise known as the nasal cycle, as for example disclosed in Shannahoff-Khalsa (1993, supra) and Werntz et al (1983, *Human Neurobiol.* 2:3943, which is incorporated herein by reference.

Alternating cerebral hemisphere activation may be determined by EEG recordings as for example disclosed in Shannahoff-Khalsa (1993, supra) and Werntz et al (1983, supra).

Also contemplated, as a measure of interhemispheric switch rate is alternation of performance in hemisphere specific functions such as verbal and spatial abilities (Shannahoff-Khalsa, 1993, supra; Klein and Armitage, 1979, *Science* 204:1326-1328, incorporated herein by reference).

Suitably, the method is further characterised by the step of processing each of the signals relating to interhemispheric alternation to convert these signals into digitised signals, and storing the digitised signals for subsequent use.

In preference, the step of determining the rate of interhemispheric switching is further characterised by dividing the number of signals corresponding to interhemispheric alternation by the total time the subject is under test. For example, in the case of perceptual rivalry referred to above, the interhemispheric switch rate may be calculated by dividing the number of perceptual switches by the total time of rivalry. Preferably, in the case of binocular rivalry such calculation excludes mixed or indeterminate percepts.

The step of determining interhemispheric switch rate may further include a practice period wherein the subject becomes familiarised with the test. Suitably, this period is not taken into account when determining the rate of interhemispheric switching.

Suitably, presence of the schizophrenic disorder subtype as herein described is diagnosed, or a predisposition thereto is suggested, when the interhemispheric switch rate of the subject is equal to a corresponding reference switch rate associated with the schizophrenic disorder subtype. In such a case, the corresponding reference switch rate may correspond to a predetermined average range of interhemispheric switch rates in subjects having the schizophrenic disorder subtype. In contrast, absence of the schizophrenic disorder subtype may be diagnosed, or predisposition thereto discounted, if the above criteria are not satisfied and/or when the interhemispheric switch rate of the subject is equal to a corresponding reference switch rate associated with normal or control phenotype. In such a case, the corresponding reference switch rate may correspond to a predetermined average range of interhemispheric switch rates in non-clinical control subjects.

In the case of an interhemispheric switch rate determined by binocular rivalry, presence of the schizophrenic disorder subtype is diagnosed, or a predisposition thereto is suggested, preferably when the rate of perceptual alternation in the subject is in the range of between is in a range from 2.0. Hz to 10.0 Hz, more preferably, the rate is in a range from 2.5 Hz to 5.0 Hz, most preferably, the response duration is in a range from 3.3 Hz to 5.0 Hz.

Preferably, the stimulus for binocular rivalry is moving gratings.

Conversely, absence of schizophrenia or schizophrenic disorder subtype may be diagnosed, or a predisposition thereto discounted, when the rate of perceptual alternation is below 2.0 Hz. Preferably, the stimulus for binocular rivalry is moving gratings.

For the above diagnoses or predispositions, the stimulus which invokes binocular rivalry in the test subject preferably comprises moving gratings.

Apparatus for Diagnosis of a Schizophrenic Disorder

The invention also provides an apparatus and method of using an apparatus for diagnosing schizophrenia, or schizophrenic subtype, or predisposition thereto as herein described. The apparatus is similar to an apparatus described in International patent application WO 99/63889, incorporated herein by reference.

The apparatus of the present invention comprises a monitoring means for monitoring interhemispheric switching in a test subject; a switching means for switching an image between right and left eyes for producing a dichoptic reversal effect; and processing means for determining an interhemispheric switch rate and for comparing said switch rate with a predetermined data set for providing diagnosis of presence or absence of the schizophrenic disorder subtype or predisposition thereto.

The monitoring means suitably comprises means for presenting different viewing images separately to each eye and recordal means for recording when the subject perceives a change in the viewed image.

Suitably the different viewing images are a moving horizontal grating presented to one eye and a moving vertical grating presented to the other eye. Alternatively, the different viewing images comprise a stationary horizontal grating presented to one eye and a stationary vertical grating presented to the other eye. Other visually distinct images, such as mentioned in the prior art relating to binocular rivalry, can also be employed.

The monitoring means may incorporate a liquid crystal shutter before each eye. The liquid crystal shutters allow the field of view of each eye to be superimposed so that the different viewing images are presented at the same retinal location of each eye. Alternatively, the monitoring means may comprise a 3D head mounted display as described in Example 2.

The recordal means for recording perceived change is suitably a subjective device in the form of an indicator means activated by the test subject when a change is perceived. Preferably, the recordal means is an objective device that records eye movements as an indicator of which image is being perceived. Alternatively, steady state visual evoked potentials may be measured to provide an objective indication of the perceptual alternation.

The processing means suitably includes timing means and means for receiving signals from the recordal means indicative of perceptual change. Interhemispheric switch rate is calculated by dividing the number of perceptual switches by the total time of perceptual rivalry.

The apparatus may also include change means for inducing a change in ratio of total time spent perceiving left eye's presented image versus right eye's presented image. The change means may be a caloric vestibular stimulation means, trans-cranial magnetic stimulation means, contrast altering means, or other means known to produce a change in the interhemispheric switch rate.

Use of Diagnostic Method to Identify Genetic Markers Linked to Schizophrenia

Also contemplated is a process for identifying one or more genetic markers associated with a schizophrenic disorder subtype as herein described, including the steps of testing respective members of one or more pedigrees affected by the schizophrenic disorder subtype using the method of the invention, identifying members having the schizophrenic disorder subtype or predisposition thereto; and conducting genetic linkage analysis on the identified members to identify the or each genetic marker associated with the schizophrenic disorder subtype.

Linkage analysis is well known to those of skill in the art. Exemplary protocols which may be used for this purpose include, but are not limited to, those disclosed in Dracopoli et al (1994, "Current Protocols in Human Genetics", John Wiley and Sons Inc., USA), Ott, J. (1991, "Analysis of Human Genetic Linkage"Johns Hopkins University Press), and Adams et al. (1998, Am. J. Hum. Genet. 62:1084-1091), which are incorporated herein by reference.

The invention also contemplates linkage studies carried out on non-affected individuals i.e. non-pedigree members. In this regard, one subset of the non-affected individuals will have fast interhemispheric switch rates and another subset will have slow interhemispheric switch rates. The application of linkage analysis to these subsets will be advantageous in identifying molecular markers linked to switch rate (a quantitatively varying trait). These markers may then be employed for the identification of molecular markers linked to the schizophrenic disorder subtype defined herein.

The invention also extends to the genetic marker(s) obtained by the aforementioned process.

Use of Diagnostic Method to Identify Candidate Therapeutic Agents

The invention also provides a process for identifying a candidate therapeutic agent for alleviating schizophrenia, including the steps of measuring first interhemispheric switch rate in a test subject, administering or applying the candidate therapeutic agent to said test subject, measuring second interhemispheric switch rate in the test subject, and identifying a candidate therapeutic agent if said second interhemispheric switch rate is faster than said first interhemispheric switch rate. Suitably, the test subject includes, but is not limited to an animal including a human, brain tissue thereof or brain cell(s) thereof.

Any suitable method may be used to determine interhemispheric switch rate. For example, methods hereinbefore described may be used in the case when the test subject is a human or animal other than human. Alternatively, when the test subject is an animal other than human, electrical activity of brainstem or hypothalamic neurones associated with interhemispheric switching may be measured. This particular technique may also be used with brain tissue or brain cells. An example of a method which uses such measurement of electrical activity in vitro and/or in vivo is described by Schaap et al (1997, Brain Res. 753:322-327) which is incorporated herein by reference.

The invention also extends to a process for identifying a candidate therapeutic agent for alleviating schizophrenia, including the steps of measuring first perceptual rivalry rate in a test subject, administering or applying a test compound to the test subject, measuring second perceptual rivalry rate in the test specimen, and identifying a candidate therapeutic agent if said second perceptual rivalry rate is faster than said first perceptual rivalry rate. Preferably, said perceptual rivalry is binocular rivalry. Suitably, the test specimen is a human or animal.

Use of Diagnostic Method to Treat Schizophrenia Patients

The invention further provides a method of treating a patient with schizophrenia, said method comprising the steps of determining an interhemispheric switch rate of the patient, comparing said interhemispheric switch rate with a range of reference interhemispheric switch rates associated with schizophrenia; and administering to said patient a pharmaceutically-effective dosage of a schizophrenia treating drug when said interhemispheric switch rate is in said range. Preferably, the interhemispheric switch rate is determined by perceptual alternation more preferably binocular rivalry. In the latter case, the drug is administered to the patient when the alternation rate is above 2.0 Hz, more preferably below 0.4 seconds.

The invention also provides a method for treating a patient with a subtype of schizophrenia diagnosed when the patient can perceive binocular rivalry when the dichoptic reversal rate is greater than 4.0 Hz, more preferably, the dichoptic reversal rate is greater than 7.5 Hz, even more preferably, the dichoptic reversal rate is greater than 15.0 Hz and most preferably, the dichoptic reversal rate is greater than 30.0 Hz.

EXPERIMENTAL RESULTS

All observers, regardless of diagnosis, showed binocular rivalry under standard rivalry conditions. They reported successive percepts of a moving horizontal grating or a moving vertical grating (dominance periods) and, less frequently, a blend of horizontal and vertical gratings or a plaid, crosshatch, grid or basket weave (non-dominance periods). This pattern of perceptual alternation is illustrated for one individual from a control group in the top sample of FIG. 1. Periods of horizontal dominance appear as blocks above the time line, periods of vertical dominance as blocks below the line, and periods of the blended or plaid percept as blocks straddling the line.

This pattern of perceptual alternation was seen in all individuals under the standard rivalry conditions (no dichoptic stimulus alternation, DSA). There were, however, individual differences in the rate of perceptual alternation (see Table 2) and in the proportion of time spent reporting the blended percept ("plaid, basket weave, crosshatch"), from 2% to 69%.

Under DSA conditions, patterns of responding were evident. With 3.75 and 7.5 Hz DSA, the samples in FIG. 4 show horizontal switching with vertical at a very high rate, consistent with the flickering changing orientations presented to either eye. For 15 and 30 Hz DSA plaid was reported consistently, as though these even more rapidly flickering orientations had fused. The flicker-like response pattern or the plaid reports were quite typical for control observers, although four controls continued to report periods of dominance with 3.75 Hz DSA. Rivalry has been reported previously in normal observers under DSA conditions by Logothetis and coworkers (Logothetis et al., 1996b).

FIG. 5 illustrates the perceptual alternations reported by an individual patient, plotted using the same conventions as in FIG. 4. Periods of horizontal or vertical perceptual dominance alternating with plaid were reported by patients as well as by controls in the standard rivalry conditions. Under conditions of DSA, however, the pattern for schizophrenic patients diverged from that for controls. Periods of horizontal or vertical dominance were still reported prominently during DSA, even at rates so high that none of the experimenters (and very few non-patients) reported seeing anything other than the blended plaid percept.

FIG. 10 shows individual data for mean dominance period (MDP) in the two groups plotted as a function of the percent time reporting plaid under standard rivalry conditions (0 Hz DSA) and at 3.75 Hz DSA. During standard rivalry MDP is negatively correlated to the percentage of time reporting plaid in both groups, although there are two outliers in the patient group. With 3.75 Hz DSA the MDP is reduced in both groups. In controls the MDP is still negatively correlated to reports of plaid but in the patients there is no correlation.

Most controls reported rapidly flickering percepts at lower rates of DSA and long periods of plaid at the higher rates. By contrast, many patients reported long horizontal or vertical dominance periods at each DSA rate despite the fact that the stimuli were alternating at rates up to almost two orders of magnitude faster than their endogenous rivalry rate. One of 18 controls and 11/24 patients reported perceptual dominance at rates higher than 3.75 Hz DSA. Significant differences in performance in the groups were revealed at all rates of DSA (see Table 2).

Because the two groups have considerable differences in cognitive ability and processing speed, it was important to show that reports of perceptual dominance were not a consequence of random button pressing. Table 3 demonstrates that while the accuracy of the patients is significantly less than that of the controls, there is no relation between response accuracy and reports of rivalry.

Inspection of the data suggested that individual performance at a particular DSA rate could be categorized as one of three response types: plaid, rivalry, or flicker. Cutoffs used to define these three states were 1) plaid, % plaid>90; 2) rivalry, MDP>0.5 sec and % plaid<90; and 3) flicker, MDP<0.5 sec and % plaid<90. FIG. 11 shows the distribution of these response types as a function of DSA rate in the two groups. The control group made relatively sharp transitions from rivalry to flicker at 3.75 Hz DSA and from flicker to plaid at 15 Hz DSA. The patients are more heterogeneously distributed. Relatively equal numbers of patients show rivalry, flicker and plaid at DSA rates between 3.75 and 15 Hz. The distributions of response type were significantly different between the groups at all DSA rates (3.75 Hz DSA, $\chi^2(2)=6.3$, $p<0.05$; 7.5 Hz DSA, $\chi^2(2)=15.6$, $p<0.0005$; 15 Hz DSA, $\chi^2(2)=7.9$, $p<0.02$; and 30 Hz DSA, $\chi^2(1)=6.9$, $p<0.01$].

Anatomy and Schizophrenia Sub-Groups

The patients who demonstrated rivalry with at least one DSA rate (n=16, the SR group) had more rightward anterior cerebellar asymmetry ($t=4.2$, $p<0.0005$) than the patients who never reported rivalry with rapid DSA (n=8, SNR). For each DSA rate, the individuals who demonstrated rivalry had greater rightward cerebellar asymmetry [3.75 Hz DSA, $t(20)=3.47$, $p<0.005$; 7.5 Hz DSA, $t(21)=3.87$, $p<0.001$; 15 Hz DSA, $t(19)=2.65$, $p<0.02$; 30 Hz DSA, $t(20)=2.51$, $p<0.025$]. The SR group had smaller left anterior cerebellar lobes ($t=2.7$, $p<0.015$) than the SNR group. Three control observers reported rivalry at one DSA and one control observer reported rivalry at three DSA rates. A distribution of rivalry report number was relatively flat for the patients with schizophrenia (Table 4). A discriminant analysis using anterior cerebellar asymmetry as a classifier correctly identified 88% of the SR and SNR groups [$F(1,22)=17.42$, $p<0.0004$]. In the patient group but not the controls, there is a significant relationship between the MDP with 3.75 Hz DSA and the asymmetry of the anterior cerebellar vermis, as shown in the left panels of FIG. 13. The right panels of FIG. 13 show how the cognitive measure phonological decoding correlates with asymmetry of the anterior cerebellar vermis, a positive relationship for schizophrenic patients but a weakly negative one for controls.

The SR group had marginally smaller left temporal plana ($t(21)=$) 1.7, $p=0.09$) than the SNR group [3.75 Hz DSA, $t(21)=3.16$, $p<0.05$; 7.5 Hz DSA, $t(21)=1.6$, $p=$n.s.; 15 Hz DSA, $t(21)=2.10$, $p=0.05$; 30 Hz DSA, $t(21)=0.94$, $p=$n.s.]. In the patients but not the controls, there was a significant relationship between MDP with 3.75 Hz DSA and the size of the left temporal planum, as shown in the left panels of FIG. 14. The right panels of FIG. 14 show how text comprehension correlates with the length of the left planum temporale, with a positive relationship for patients but none for controls.

In summary, patients who report periods of perceptual dominance with rapid DSA are more likely to have a small left planum temporale, a small left anterior cerebellar vermis, and a lower single word reading score than patients without perceptual dominance under these conditions. Since these groups do not differ in the accuracy of reporting their experiences, it appears that this cluster of perceptual, anatomical, and cognitive characteristics may characterize a useful biological endophenotype.

The response measures used are quantitative and enable objective comparisons between different individuals, but they rely on an ability to report subtle perceptual changes that could be argued might be compromised in schizophrenia. This issue was addressed with the training procedure and with signal detection analysis, which provided likelihood ratios that the individuals' reports were correct relative to being wrong. All patients had likelihood ratios greater than a 1:3 ratio for random guessing, as assessed in the pre- and post-experiment "movies", and there was no relation between these likelihood ratios and the probability of reporting perceptual dominance (see Table 3). The validity of the schizophrenic reports of their perceptions is further supported by the fact that they showed systematic trends like controls in the proportion of rivalry, flicker and plaid as DSA frequency increased. Additional evidence that rivalry with rapid DSA represents an actual phenomenon in schizophrenia is provided by the fact that the length of rivalry dominance periods is lawfully related to measures of left hemisphere and cerebellar anatomy (see FIGS. 6 and 7). It seems unlikely that such relationships would emerge as a result of random button presses. The inventors also described each epoch's results to the participant immediately after the data were collected in order to elicit their opinion of how well the data represented what they saw. Although this step was influenced to an unknown degree by demand characteristics, it allowed identification of rare pronounced mismatches between button press responses and what the participant said they recalled having seen.

A number of visual traits have been reported to be significantly altered in schizophrenia. These include reductions in pre-pulse inhibition (Lipp, 1998), alterations in cognitive tasks involving attention (Javitt, 2000) and reductions in the gain of smooth pursuit eye movements (Chen et al., 1999). It is unlikely that abnormal eye movements are responsible for the stable rivalry because during DSA at 7.5, 15 or 30 Hz there is not sufficient time during each phase of stimulus exposure to overcome the latency for initiating smooth pursuit eye movements, let alone to acquire the moving target. In addition, the sign of the schizophrenia-control difference is opposite to what would be expected from reduction in ability to track visual targets. Reported differences in smooth pursuit cannot explain the temporal performance of the schizophrenic visual system at the other alternation rates.

There is a longstanding controversy about the neural locus of rivalry. Studies in monkeys, who cannot verbally report their perceptual alternations but whose nonverbal behaviors seem reliably to match responses made by humans, are proving informative. Early in the visual pathway there are many neurons whose visual responses contradict the monkey's reported experience, while at "very high" levels in the visual pathway (e.g. inferotemporal cortex) there are neurons whose behavior switches with the monkey's perception (Sheinberg, 2001). Scanning studies using fMRI and MEG have tended to support the new evidence that binocular rivalry is a high level phenomenon with participation of widely separated regions from visual to frontal cortex (Lumer, 1998; Srinivasan, 1999; Tong, 2001). Some mapping studies maintain that primary visual cortex is the site of rivalry (Tong, 1998; Polonsky, 2000), although the possibility has not been excluded that these results could be the consequence of top-down influences from higher levels of the visual system.

Not being bound by theory, the present results support binocular rivalry as resulting from more global processing at higher levels and in widespread brain regions, perhaps coordinated on a hemispheric basis (Miller et al., 2000), with feedback to early visual processing (Blake, 2002). A tendency to rival at high DSA rates may reflect an altered balance between visual cortex, which is capable of following high rates of stimulus change (Pettigrew, 2001), and slower frontal regions. It seems unlikely that processing in the primary visual cortex of control and schizophrenic individuals would be so different that it could explain the present marked perceptual differences without also affecting the patients' visual acuity and myriad other functions that rely on V1. This view is consistent with a number of studies that have suggested a diminished role for frontal regions with a greater relative emphasis on processing in posterior brain regions in schizophrenics [e.g. Tononi and Edelman; Andreas Meyer-Lindenberg, M.D., and Karen Berman, M.D., report on their PET (positron emission tomography) study, published online Jan. 28, 2002, in Nature Neuroscience].

This interpretation of individual differences in the balance of anterior versus posterior processes leaves room for the possibility that reduced frontal activity, despite the usual negative connotations, might be accompanied by superior temporal performance in the rivalry of schizophrenic relatives and others with this trait. This stresses the positive aspects of the high-speed processing that we found to be so prominent in schizophrenia. Relative roles of frontal and visual cortex could be directly checked using scanning methods (fMRI, PET, MEG or multi-electrode VEP) while individuals experienced rivalry.

Alternatively, it could be argued that survival of binocular rivalry with high rates of dichoptic alternation reflects a relative failure of the rivalry system to be influenced by fast transients (perhaps by missing or under-sampling the stimulus alternations) in some schizophrenics. Recent work that allows flicker detection and rapid dichoptic alternation to compete in binocular rivalry has raised the question of whether the magnocellular system is involved in the failure of rivalry at high temporal frequencies (Silver, 2001). Deficits in the magnocellular system have been reported in dyslexia, for example (Livingstone et al., 1991). The anatomical variables presently measured have been found to predict reading skill in a variety of populations (Rumsey, 1998; Eckert et al., 2001; Leonard et al., 2001a). Individuals with dyslexia whose text comprehension is considerably superior to their single and pseudo word reading skills have large left plana temporale and leftward anterior cerebellar asymmetry. Individuals with poor reading skills who do not have a discrepancy between comprehension and coding are more likely to have small left plana temporale and rightward cerebellar asymmetry. As shown herein, patients with schizophrenia who rivaled with rapid DSA had the anatomical and cognitive characteristics of this latter group. The fact that the patients with schizophrenia who demonstrate rivalry with rapid DSA have impaired cognitive ability in addition to their phonological decoding deficits does not support a simple relationship among magnocellular deficit, rivalry, cognitive and reading skills. Notably, the four control observers who rivaled with rapid DSA did not have reading or cognitive deficits, and few patients with schizophrenia, regardless of rivalry status, have a dyslexic profile.

Many neurobiological markers of illness are found in relatives of schizophrenics as well as in the patients themselves. The binocular rivalry alternation rate is highly repeatable in individuals (test-retest r=0.85) and also appears to have high heritability based on a comparison of monozygotic and dizygotic twins so that rivalry measures appear suitable for diagnostic and endophenotype studies.

Throughout this specification, unless the context requires otherwise, the words "comprise", "comprises" and "comprising" will be understood to imply the inclusion of a stated integer or group of integers but not the exclusion of any other integer or group of integers.

In order that the invention may be readily understood and put into practical effect, particular preferred embodiments will now be described by way of the following non-limiting examples.

EXAMPLE 1

Subjects

Data were obtained from 24 individuals with chronic schizophrenia and 18 normal volunteers. The groups were balanced on age, sex, a quantitative measure of hand dominance and parental socioeconomic status (see Table 1).

Inclusion criteria for the patients with schizophrenia. (1) A diagnosis of schizophrenia which satisfied the criteria for the Structured Clinical Interview for DSM-IV (SCID) (First, 1996) (2) A stable condition with no major changes in symptomatology or psychosocial adjustment for two months prior to MRI scan and testing. (3) A likelihood ratio (hits/false alarms) of better than 3:1 in a signal detection task designed to reproduce the perceptual switches of binocular rivalry (see below and Table 3).

Exclusion criteria included: (1) any history of CNS illness, (2) head injury leading to loss of consciousness for greater than 5 minutes, (3) electroconvulsive therapy, (4) heavy alcohol, street drug or steroid use in the past 3 months, and (5) comorbidity with other psychiatric disorders. Alcohol and drug lifetime histories were assessed and medical records reviewed for information to document alcohol and drug problems (including drug screening reports). The Michigan Alcohol Screening Test (MAST) provided an estimate of the pathogenic significance of alcohol use. Demographic information collected included age, sex, handedness (with a modified Edinburgh questionnaire; (Briggs and Nebes, 1974), education, work history and enough information to assess socioeconomic status (SES) of the parents, as estimated by the Hollingshead-Redlich 4-factor Index (Hollingshead, 1975).

Controls. Controls were recruited through flyers and a notice in the regional utilities company newsletter. Matching criteria were age, gender, a quantitative measure of handedness, and parental SES. Volunteers were interviewed (SCID) and were excluded if they were positive on any of the exclusion criteria described for the schizophrenia group or had a family history of psychosis or a personal history of psychiatric disorder. As with the schizophrenia sample, the MAST and a lifetime history of alcohol and drug use were obtained, in addition to the same demographic information. A further sample of 68 undergraduate college students provided additional normative data on binocular rivalry under conditions of DSA. Informed consent was obtained from all participants as approved by the institutional review boards of the University of Florida and the Malcolm Randall Veterans' Affairs Medical Center.

EXAMPLE 2

Rivalry Procedure

The technique for eliciting binocular rivalry was similar to that already published, with two small targets presented foveally so that the right eye saw, for example, only a drifting horizontal grating and the left eye saw only a drifting vertical grating, in the same location (Pettigrew and Miller, 1998). The additional modification used here was dichoptic stimulus alternation (DSA), as described below.

Display. PC compatible computers equipped with ATI mach 64 video chipsets (eMachines eTower 333cs) ran custom software (written by KDW) to generate the rivalry stimuli in a frame sequential format, to measure responses, and to provide user interfaces. In the frame sequential format, odd numbered frames are presented to one eye while even numbered frames are presented to the other eye. The software was triggered by the video vertical synch, which caused one of two pages of the video RAM to be displayed. Then the software copied the next stimulus to be displayed into the non-displayed page of video RAM, read and stored the status of mouse buttons, and waited for the next vertical synch to exchange which page of video RAM was displayed. The observer wore a head-mounted display (iGlasses) with SVHS resolution, which was synchronized to the frames generated in an SVGA graphics mode (1024×768×256 at 60 Hz non-interlaced) by an AverMedia Averkey scan converter. The Virtual I-O iGlasses 3D head-mounted display has separately driven LCD displays (180,000 pixels) for each eye, giving resolutions of 225×266.

Figure 1:
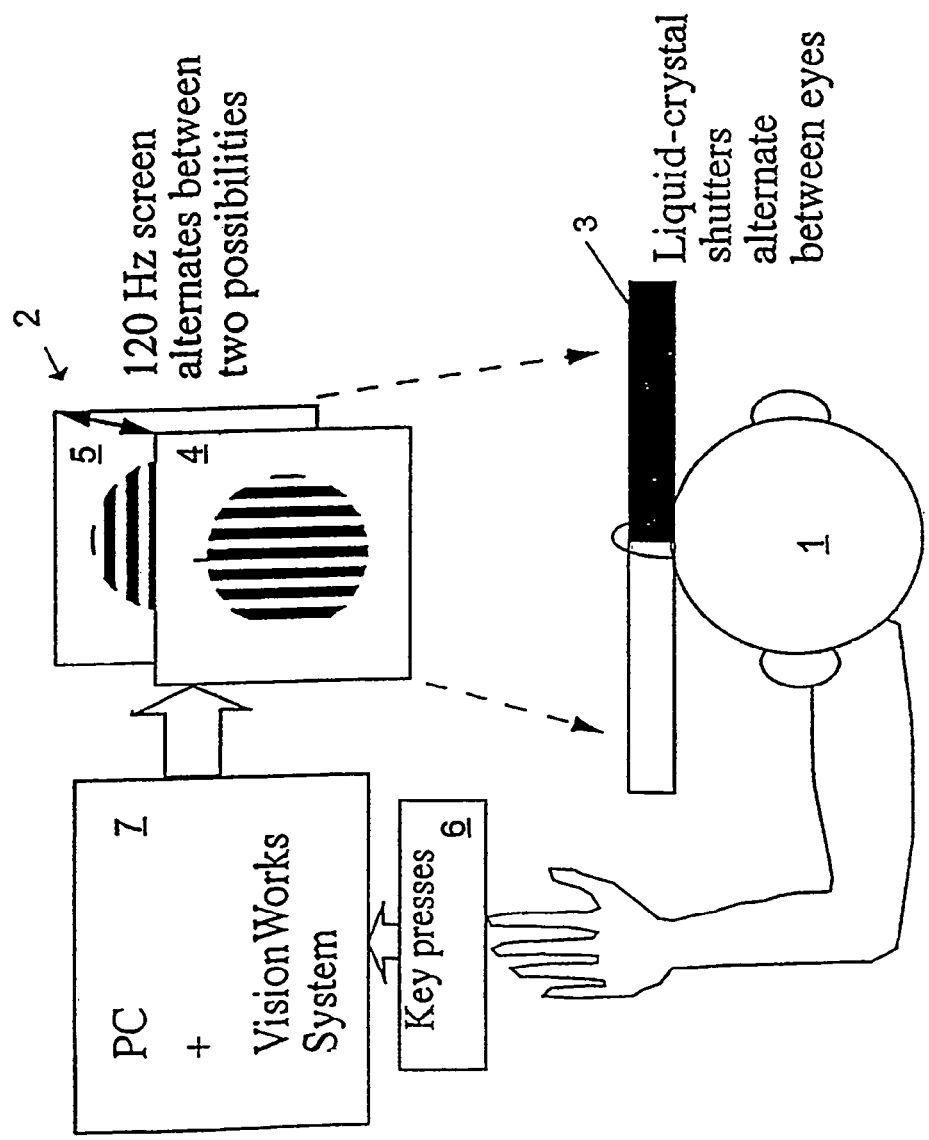
Figure 2:
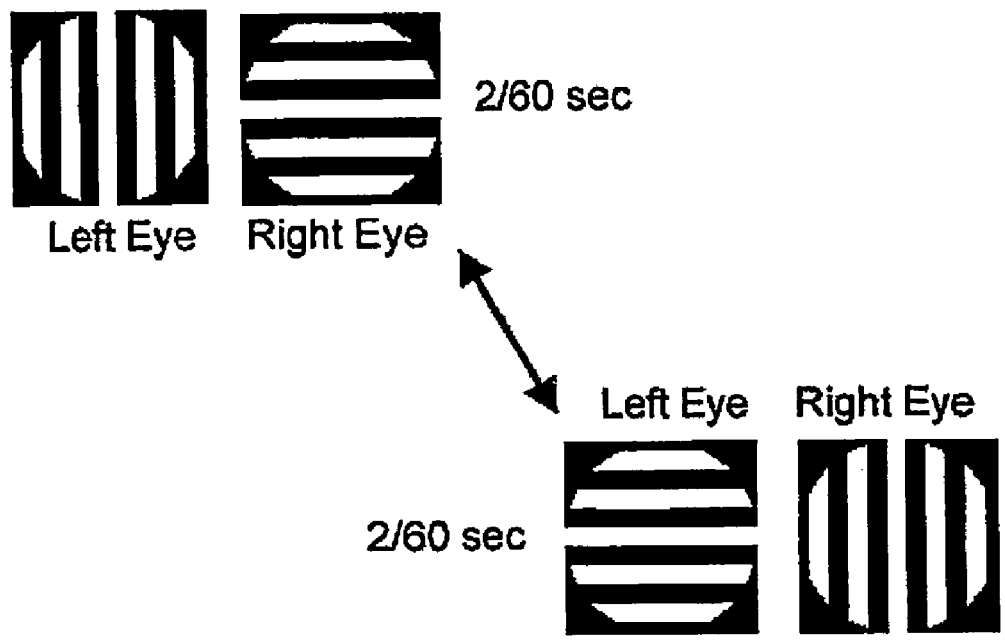
FIG. 2 shows images used with a dichoptic reversal method described herein. The images may be displayed with the apparatus shown in FIG. 1.
Figure 3:
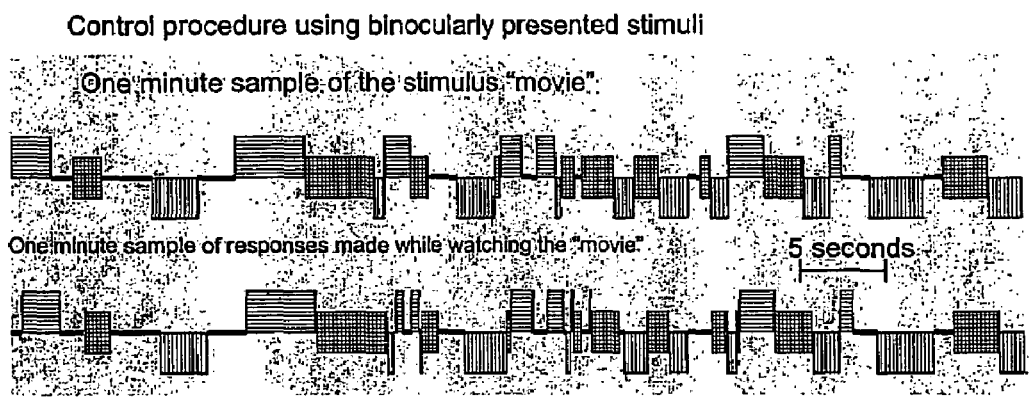
FIG. 3 shows a tracing for control procedure using binocular presented stimuli.

An apparatus shown in FIG. 1 may also be used for measuring a rate of binocular rivalry. Binocular rivalry is tested with a subject 1 seated three meters from a computer monitor 2 and wearing liquid crystal shutter goggles 3 to enable the presentation of vertical moving lines 4 to the left eye and horizontal moving lines 5 to the right eye. The stimuli subtend 1.5 degrees of visual angle with a spatial frequency of 8 cycles/degree moving at 4 cycles/second. The subject 1 presses one of three response buttons 6 to indicate their perceptual state (horizontal, vertical or mixed/indeterminate percepts). The response buttons 6 may be located on a computer mouse.

PC compatible computers equipped with ATI mach 64 video chipsets (eMachines eTower 333cs) run locally written software to generate the rivalry stimuli, measure the subject's responses, and provide user interfaces. One of these PCs provides a display for the subject to view on a 14 inch XGA resolution monitor (0.25 mm dot pitch Triniton), which the subject views through Nuvision liquid crystal shutter glasses.

The glasses are synchronized to the video vertical synch by means of a dongle attached to the VGA port which serves as a pass-through to the monitor, and which also passes the vertical synch to infrared light emitting diodes and associated circuitry. Pulses from the IR LEDs cause the liquid crystals to switch from transmitting to occluding every other video frame (viz, for frame sequential presentations).

Stimuli. The stimuli consisted of white binocular fixation guides centered within which was a 1 deg disk filled with a moving grating. These fixation guides consisted of (1) a rectangular frame drawn around the borders of the 12×9 deg screen, (2) a circle 9 deg in diameter centered on the screen center, and (3) a plus-sign shaped crosshair at the screen center for which the centermost 3 deg horizontal and vertical were removed. All stroke widths for the fixation guides were about $\frac{1}{16}$ deg wide. The 1 deg disk at the screen center was filled with 5 cycle per deg square wave gratings undergoing shifts of spatial phase through $\frac{360}{16}$ deg of phase angle every $\frac{1}{30}$ sec, or motion through one cycle in $\frac{16}{30}$ sec, approximately 2 cycles/sec. The disk could be presented binocularly (same grating orientation in both eyes) or dichoptically (different grating orientations in the two eyes).

Training in the reporting task. Observers were instructed verbally while they watched binocular stimuli (both eyes received the same stimulus, there was no rivalry) while holding the computer mouse in both hands. These binocular stimuli looked exactly like the experimental stimuli (save that the experimental stimuli used dichoptically presented disks). Superimposed on this pattern was a grey drawing of a computer mouse. When the grating was horizontal and moving downward, the left button part of this mouse picture contained three horizontal red stripes (separated by black stripes) while the right button was greyed. The left button on the mouse physically held by the observer also had three red horizontal stripes made of foam tape so as to be tactually distinctive for the left thumb. The observers were instructed to move their thumb along and across the stripes to feel this shape cue for the horizontal report button. They were also instructed to keep this button held down for the entire time that they saw horizontal stripes in the disk. The computer beeped about 4 times per sec during this training demonstration unless the observer held down the correct button (and no other), which silenced the beeps. The observer was then shown vertical stripes moving rightward filling the disk, and the left button on the mouse picture became greyed while the right button part displayed three red vertical stripes. These corresponded to three red foam tape stripes attached to the right button of the mouse held in their hands. Again, the observers were instructed to move their thumb along and across the stripes to feel this shape cue, and reminded to hold down the right button for as long as they saw vertical stripes. Next the disk was filled with superimposed horizontal and vertical (a plaid or grid), and both buttons on the mouse picture changed to red stripes. The observer was told to report this blended or plaid appearance, which moved down to the right in about the four o'clock direction, by holding down both mouse buttons. Lastly, the disk was filled with a homogeneous field (blank) and both mouse picture buttons became grey. The observer was instructed to let up both buttons unless the disk was completely filled with horizontal or vertical or plaid, and, when unsure, to press nothing.

Signal detection analysis of reporting accuracy. The task training was evaluated with a "movie" that simulates rivalry alternation using binocular stimuli. Stimulus durations were sampled at equal probability intervals from a cumulative gamma distribution (Levelt, 1965), and the disk content (horizontal, vertical, plaid, blank) randomly assigned that duration, with the proviso that two durations with the same content could not occur in immediate succession. A 90 sec sequence of such quasi-randomly selected stimuli changed unpredictably in pattern content and duration, but in such a way that 25% of the time each pattern appeared. A software program scored the observer's button presses during the "movie" were scored correct or incorrect (by software) depending upon which stimulus pattern preceded pressing of the button(s). These calculations were carried out for time lags between stimulus and response from 0.3 to 3.0 sec in 0.1 sec steps, comparing button press to stimulus each $\frac{1}{60}$ sec. Random guessing produces 25% correct (hits) and 75% wrong (false alarm) choices. An observer was not allowed to begin the experiment unless three of the four pattern/response types reached a criterion of least 50% hits, except for one patient. The "movie" could be repeated if further training was found to be necessary, which was done for one control and two patient participants. The "movie" was usually shown again at the conclusion of the experimental procedure to detect any possible declines in response reliability. Such declines were not found.

The training and evaluation procedures could generally be completed in about 5 min, but patients with compromised cognitive ability could require up to 15 min to reach criterion performance. Typical performances were 85% to 95% hits with 5% to 15% false alarms, by control observers and 70% to 90% hits with 10% to 30% false alarms by patients with schizophrenia. Two patients were excluded from further participation due to failure to achieve criterion performance within 20 min.

Experimental Sequence. The test subject was presented traditional binocular rivalry for 4 to 9 min (in six epochs) to obtain the endogenous perceptual alternation rate, and presented dichoptic reversal stimuli at 3.75, 7.5, 15, and 30 reversals per sec for 2 min at each rate in two ~1 min epochs (14 epochs per observer). Order of presentation of traditional rivalry and the four reversal rates was counterbalanced within observer. At the end of each epoch a graph of the responses was displayed. The experimenter described in words the general features shown in the graph in order to verify that these recorded responses were representative of the observer's perceptions. In a small number of cases (7 out of 524 epochs) the observer did not confirm that the recorded responses were representative, so a comment was entered into the data record and those epochs were excluded from later analysis. One patient failed to complete testing at 7.5 Hz, 2 at 3.75 Hz and 30 Hz, and 3 at 15 Hz. The experimental procedure was completed in 25 to 40 min by controls and by some patients, although those with cognitive impairment required more time and, sometimes, were tested in two or three sessions on separate days.

EXAMPLE 3

Assessment of Schizophrenia Symptoms

Schizophrenia symptoms may be assessed with the Positive and Negative Syndrome scale (PANSS) (Kay, Opler et al. 1992), incorporated herein by reference, an instrument that provides reliable quantitative ratings of 30 symptoms, which are divided into positive, negative, and general psychopathology subscales. Symptoms are rated on a 1-7 point scale from absent to extreme. The instrument contains measures of all the major psychotic symptom areas of interest except for inappropriate (incongruent) affect. Inappropriate affect is rated according to a scale modification (from 1-6 to 1-7 points) of the criteria used in the SAPS (Andreason 1984), incorporated herein by reference.

A range of symptoms, with addition of inappropriate affect, samples a major symptom clusters derived from factor analysis of numerous data sets. Clinical features of schizophrenia hypothesized to provide information regarding a course and severity of illness is systematically recorded. These include treatment resistance, extrapyramidal symptoms, age of onset, deficit syndrome, stability of current clinical state, type of medication at time of testing and premorbid functioning. For treatment resistance, research criteria is used of Kane and the Clozaril collaborative group as presented by Meltzer et al (Meltzer, Rabinowitz et al. 1997), incorporated herein by reference. The criteria includes: (1) persistent moderate to severe delusions, hallucinations or thought disorder or (2) pervasive negative symptoms, such as withdrawal, anhedonia, poverty of thought content, a deficit in volition and lack of energy, despite at least three trials of typical neuroleptic drugs for at least six weeks at adequate doses. Neuroleptic-responsive patients are those who at most had mild positive and negative symptoms during the most recent course of neuroleptic treatment.

The stability of current clinical state will require clinical records and interview of families, caretakers and other available informants indicating no major changes for two months and a recording of current level of active symptoms commensurate with the records. When this is unclear from records, clinicians, and/or caretakers or significant others, a baseline will be established and the patient revisited after 2 months. The age of onset will be estimated by reviewing records asking the patient and available family and other significant persons. The Abnormal Involuntary Movement Scale (AIM)(National Institute of Mental 1975), incorporated herein by reference, is used to measure extrapyramidal symptoms.

Deficit syndrome is rated using the Schedule for the Deficit Syndrome, 1993, incorporated herein by reference, which provides a global severity rating of 0-4.

Type and amount of medication at the time of scanning and testing is important for several reasons. Different medications produce differential responses and side effects. Medications with anticholinergic side effects may affect performance on memory tests. These measures will be collected for two reasons: (1) to determine if any of these factors affect the probability of abnormal binocular rivalry; (2) to train graduate and postdoctoral fellows in the methodology of research diagnoses.

The PANSS interview is taped so it is available for scoring, reliability training and checks, and tracing of the course of the disease over time. The PANSS is administered when, in the staff's opinion, the patient is at a level of stability compatible with tolerating the interview. As the study progresses, the distribution of symptoms in the patients in the sample will be periodically checked to ensure that a sufficient range on each symptom dimension is represented. The PI rates all patient tapes himself, usually with one or more other trained raters. Each makes independent ratings and there will be a periodic (every three months) check on the reliability. Since each case is rated by more than one rater, there is a constant review. Details of disagreements are checked against the symptom criteria and the raw data of the tape.

The scores of 20 sequential patients with PANSS interviews, scored blindly by two different raters, were analyzed for reliability between raters. The percentage agreement for the 8 positive symptoms was 92.5%, for the 7 negative symptoms was 91.4% and for the 16 general psychopathology symptoms=89.4%.

EXAMPLE 4

Cognitive Battery

Cognitive ability was assessed with the Woodcock Johnson test of Cognitive Ability (WJ-Cog) (Woodcock and Mather, 1989). These tests measure aspects of cognitive ability that emerge in factor analyses of large samples (g or broad cognitive ability, short term memory, long term retrieval, symbol matching, auditory and visual processing) (Carroll, 1993). Reading tests were also administered, since single word reading accuracy is considered a reliable estimate of premorbid verbal intelligence (Weickert et al., 2000). Three subtests from the Woodcock Reading Mastery Tests-revised WRMT-R:(Woodcock, 1987) reading battery were administered: 1) Word Attack; 2) Letter Word Identification; 3) Passage Comprehension. A study of college students found that scores on these tests were not only predictive of reading disability, but were also predicted by various brain measures in regions previously implicated in schizophrenia (Leonard et al., 2001a).

Cognitive speed is measured with four tests of sensory and motor reaction times: Visual inspection time (IT) is defined as the minimum period that two vertical lines of unequal length must be visible in order for an individual to make a correct lateralization 75% of the time. Simple reaction time is the time taken to depress a suddenly illuminated button. Choice reaction time is the time taken to depress the correct choice among two simple alternatives. Odd man reaction time is the time taken to respond choose the side with only one light when 3 buttons are suddenly illuminated. In normal and reading disabled subjects, odd man reaction time and visual inspection time predict poor performance on reading and language tests. The schizophrenics in our sample regardless of rivalry subgroup performed poorly on the Woodcock Johnson tests of cognitive speed.

EXAMPLE 5

Magnetic Resonance Imaging (MRI)

Magnetic resonance imaging scan sequences were performed in a 1.5 Siemens Magnetom using a quadrature head coil: (1) a gradient echo volumetric acquisition "Turboflash" MP Rage sequence (TR=10 ms, TE=4 ms, FA=10°, 1 acquisition, 25 cm field of view, matrix=130×256, 6.03 min) that were reconstructed into a gapless series of 128 1.25-mm thick images in the sagittal plane; and (2) a traditional axial scan of 5-mm T2 and spin density weighted images separated by 2.5 mm gaps (time=8 min). Images. The scans were archived in the University of Florida Radiology Archive, were screened by a neuroradiologist for clinically significant findings, and transferred electronically to a workstation in the imaging laboratory. Headers containing identifying characteristics were removed, images were concatenated into a series, assigned a randomly chosen blind number and reformatted into 1 mm thick slices in the Talairach planes (Talairach, 1988) using programs written in PVWave (Visual Numerics, Boulder Colo.) (Leonard et al., 1998). The MRI analysis was similar for all scans. Two raters blind to subject characteristics made each measurement and differences were resolved by discussion.

There have been many reports of group differences in volumetric analyses in schizophrenia but few findings are either sensitive or specific (Heinrichs, 2001). The brain measures reported here are those that previous work has identified as conferring a risk for cognitive and reading impairment (Leonard et al., 1999) (Eckert et al., 2001; Leonard et al., 2001b).

Cerebral hemispheres. The volume of each cerebral hemisphere was measured by tracing the area enclosed by the dura on every fourth sagittal image, and summing the averages of adjacent areas after multiplying by the width of the inter image gap. The midsection was traced twice and half the slab volume added to each hemisphere. (Volumes calculated with this method correlate 0.98 with volumes calculated from measurements of every image). This measure includes intra sulcal CSF and thus reflects original cerebral capacity before the onset of age-related cortical loss. Inter-rater reliability of this measure is >0.9 (intra class correlation). The coefficient of asymmetry of the cerebral hemispheres was calculated by dividing the R/L difference by the average volume of the two hemispheres. Rightward z scores are positive.

Anterior cerebellar vermis, The anterior lobes of the cerebellum were measured in sagittal images. Every 1 mm thick section on which the primary fissure could be seen was outlined and the areas added to calculate the volume in each hemisphere. As the primary fissure becomes indistinct laterally, the lateral boundary of the anterior lobe was defined as the image on which the superior cerebellar vessels disappeared. Inter rater reliability for this measurement is 0.87. The coefficient of asymmetry was calculated by dividing the L/R difference by the average volume of the two hemispheres, Leftward scores are positive.

Temporal and parietal planum. The surface area of the temporal bank of the planum (PT) was measured between the posterior boundary of the first transverse (primary) gyrus of Heschl (Heschl's sulcus), and the termination of the Sylvian fissure, which in most cases was marked by a small elevation in the PT (see FIG. 15) and a bifurcation into a descending ramus and the posterior ascending ramus, commonly referred to as the parietal planum (PP). The small posterior descending ramus which originated from a bifurcation was not included in the measure. In cases where PP originated proximally to the termination of the sylvian fissure (inverted formation) (Ide et al., 1996) the large extent of sylvian fissure posterior to PP was included in the PT measurement. The PP was measured from the bifurcation to its dorsal termination. In the small number of cases where no elevation or bifurcation marked the origin of PP, the 'knife cut' method was used (Witelson and Kigar, 1992). In cases where the sylvian fissure merged with the superior temporal sulcus or other occipitoparietal sulci, the PP and PT measurements were terminated at the point of the merge. An index of surface area was calculated by averaging the length measured between standard Talairach positions (x=46 and 56 mm) as reported previously (Leonard et al., 1993; Foundas et al., 1994; Foundas et al., 1995; Leonard, 1996).

Heschl's Gyri. The surface areas of the primary Heschl's gyrus (H1) and, when present, a second gyrus (H2) (Leonard, et al. 1998) were traced between their limiting sulci on consecutive sagittal images between x=34 and x=48. Inter rater reliabilities are 0.9 for H1 and 0.85 for H2.

Ventricles: Ventricle volumes are measured semi-automatically. A mouse-operated cursor is used to outline the region that includes every thresholded csf voxel. The histogram of voxel gray levels is stored in a file and the volume of the ventricle is calculated by totaling the number of voxels meeting the criterion for csf. The reliability of ventricles measured in this way is greater than 95%. Third ventricles measured with this method contributed significantly to discrimination of schizophrenics from controls (Leonard, Kuldau et al. 1999).

EXAMPLE 6

Data Analysis.

For binocular rivalry, the raw data consisted of the time (in msec) of each mouse click. These data were automatically entered into spreadsheets and analyzed with macros which combined epochs for similar DSA rates and extracted the mean length that horizontal, vertical, plaid, and nothing were reported. Two quantitative measures were used to characterize performance for each DSA rate: 1) Mean dominance period (MDP), total duration of horizontal or vertical responses/number of horizontal and vertical responses, and 2) percent time reporting plaid (% plaid). Rivalry, anatomical, and cognitive variables were entered into spreadsheets and analyzed with PC-SAS. Regression coefficients were calculated between variables from different domains and t tests were used to assess the significance of differences in the anatomical and cognitive domains. As the values for MDP and % plaid were not normally distributed, these distributions were compared with conservative non-parametric tests: k-sample extension of the median test, chi square ($\chi^2$), and the $\chi^2$ approximation of the Kolgomorov-Smirnov two-sample statistic for small unequal samples (Siegel, 1956).

Functional MRI

Technical limitations presently make it difficult to use fMRI to seek out a neural basis of the perceptual oscillation of rivalry, whose period of a second or so is close to the temporal limits of the fMRI technique when used for brain imaging. This limitation is greater in schizophrenic subjects whose period of perceptual oscillation is even shorter than normals.

There are, however, questions about schizophrenia and rivalry that can be addressed directly with fMRI. Sub-grouping of schizophrenics that have been identified or otherwise, may be further refined if patterns of activity in fMRI can be used to support the sub-divisions based upon rivalry, neuroanatomy and cognitive testing. In addition, fMRI could also illuminate the mechanism of the enhanced sensitivity to high-speed dichoptic alternations that has so far been found uniquely in schizophrenics in sub-group B (group SR).

There is already some Positron Emission Scanning evidence (PET) for this proposal (Tononi and Edelman 2000), which is also consonant with a widespread view that pre-frontal cortex under performs in schizophrenia (Goldman-Rakic and Selemon 1997).

MRI scans may be performed using a UF 3.0 Tesla whole body MRI scanner (GE/Signa LX).

Methods: The subject lies supine on the scanner table and their knees and neck are supported by pillows. The dome-shaped phased array head coil for transmitting and receiving radio frequencies is positioned along the body axis by a fixed pad between the coil and the top of the head, and the head is positioned left/right and up/down within the coil as symmetrically as possible. The head is stabilized in that position by wrapping the pillow from under the neck up toward the ears and also by inserting supplemental foam pads of assorted shapes to hold the head firmly yet comfortably. When the subject is ready they are land marked to the scanner's vertically projected index crosshair by aligning it with the nasion, and to the horizontally projected index crosshair by aligning to the anterior edge of the pinna.

After land marking the table transports the subject into the bore to commence scout scans which require about 3 minutes. These scouts insure that the head was positioned within a reasonably close approximation of the ideal translational and rotational coordinates so that the gradients can be prescribed. If subject positioning is not suitable then the subject is transported back out the bore and their head position adjusted. If it is confirmed that the subject is positioned correctly then a 2-d T1-weighted scan is carried out to reveal the vasculature, and a 3-d SPGR scan carried out for a high resolution structural image. These latter scans together take about 16 minutes. The structural phase of imaging ideally lasts about 20 minutes.

Functional images are then collected in a block designed experiment (described below). First, 22 to 24 slices covering the whole brain will be scanned with echo-planar imaging made sensitive to BOLD contrast (TR=2500 msec, TE=25 msec, FOV=20×20 cm, 64×64 matrix, slice thickness=6 mm, in-plane resolution=3.2×3.2 mm), to identify a smaller region of interest for subsequent high-resolution single slice acquisition. Four such scans will be done, requiring about 1 minute each, a scan for each of the four dichoptic reversal rates of stimulation.

Rivalry in the Magnet: Stimulation is provided by video rear projection using a special screen material (Aeroview 100) that retains the polarization planes of transmitted light. A plane-polarizing filter intercepts the projector beam near its exit from the lens. Frame successive sequencing of stimulus frames destined for the fellow eyes are synchronized with a liquid crystal for rotating the polarization plane. Orthogonal polaroid analyzers at subject's eyes alternately transmit or block light transmission on alternate frames, one eye being blocked while the other is not. This implementation is a re-arrangement of the polarizers and liquid crystals as used in stereoscopic shutter glasses, which leaves near the subject only a magnetically inert polarizing filter. The optically and electronically active liquid crystal which is not magnetically passive is placed well outside the bore.

High-resolution single slice acquisition uses gradient echo FLASH (TR=45 msec, TE-=30 msec, FOV=20×20 cm, 512×512 matrix, slice thickness=5 mm, in-plane resolution ~0.5 mm)(Liu, Pu et al. 2000). Scans are acquired in a block design. Each block consists of a 1 min period during which dichoptically reversing rivalry stimuli (presented at 3.75, 7.5, 15, or 30 rev/sec) or a control task or rest take place. The single slices can be acquired every 12 sec in each block. A session of six blocks (6 min) is followed by a pause to offload data (about 1 min). Four such sessions (a total of 24 blocks) are carried out. In two of the sessions the subject makes overt responses (button presses) to indicate their perceptual state, and in the other two sessions the buttons are not pressed except during the control task.

The function MRI phase of imaging ideally lasts about 30 minutes, which is about as long as is reasonable to expect for the subjects to remain still. Fortunately, usable data can still be gleaned from the scans even if all 24 blocks are not successfully imaged.

FIG. 16 shows an example of a high resolution fMRI single slice. Darkened areas (increased metallic content) show basal ganglia, and dentate and red nuclei.

Data analysis. There are new and powerful data analysis tools, such as within-condition interregional covariance analysis and temporal clustering analysis (Xiong 2000). Clustering analysis involves calculating the entropy (a multivariate statistic analogous to univariate variance) and mutual information (analogous to univariate covariance) for various subsets of voxels so as to select those subsets which interact more strongly within their own subset than with the rest of the voxel population. A subset meets this criterion when mutual information is large relative to the population entropy (their ratio is somewhat analogous to an F statistic). The efficacy of clustering analysis for discriminating SCZ scans from control subject scans has recently been shown for positron emission tomography (PET) results (Tononi and Edelman 2000) 2000). The PET scans in this paper had previously been analyzed unsuccessfully with commonly used statistical parameter mapping software, but the clustering analysis revealed regions of activation differing between SCZ and controls. Our fMRI scans will have two advantages over static PET scans, namely smaller voxels and a time course of data. Temporal clustering analysis (Liu) utilizes the waxing and waning of entropy and mutual information over time to aid further in identifying event-related activations.

Hypotheses. Voxelwise correlations (magnitude and variance of activation) with perceptual switching rate (as determined per subject per rev rate in psychophysics) predict low correlation for early visual cortical areas, increasing correlation moving anterior, as per Logothetis and colleagues' (Leopold and Logothetis 1996) single unit data that showed increasing correlation between monkey's perception and single unit behaviour as study moved anteriorly from primary visual cortex to inferotemporal cortex.

Human Subjects

The invention may assist to further delineate an endophenotype for schizophrenia derived from neuroanatomical and psychophysical measures. Subjects with DSM-IV-diagnosed schizophrenia will receive an MRI brain scan, structured interviews and testing for symptoms, cognitive profile, and a visual psychophysics measure of neural timing based upon binocular rivalry. The structured interview for symptoms will be videotaped for later scoring, and a separate informed consent form will be used for this taping. A subset of patients, chosen on the basis of their likely ability to perform the binocular rivalry tasks in the scanner, will be asked to have a functional imaging scan (in addition to the structural scan), to identify which parts of the brain are responsible for binocular rivalry and how schizophrenic subjects might differ from controls.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

The disclosure of each patent and scientific document, computer program and algorithm referred to in this specification is incorporated by reference in its entirety.

REFERENCES

Blake R (1989) A neural theory of binocular rivalry. Psychol Rev 96:145-167.

Blake R (2001) A primer on binocular rivalry, including current controversies. Brain and Mind:5-38.

Blake R, Logothetis, N. K. (2002) Visual Competition. Neuroscience 3:13-21.

Briggs G G, Nebes R D (1974) Patterns of hand preference in a student population. Cortex 11:230-238.

Carroll J B (1993) Human cognitive abilities: A survey of factor, analytic studies. Cambridge: Cambridge University Press.

Chen Y, Nakayama K, Levy D L, Matthysse S, Holzman P S (1999) Psychophysical isolation of a motion-processing deficit in schizophrenics and their relatives and its association with impaired smooth pursuit. Proceedings of the National Academy of Sciences, USA 96:4724-4729.

Eckert M A, Lombardino L J, Leonard C M (2001) Tipping the environmental playground: Who is at risk for reading failure. Child Dev 72:988-1002.

First M, Gibbon, M, Spitzer, R L, Williams, J B W (1996) The Structured Clinical Interview for DSM-IV-TR.

Foundas A, Leonard C M, Gilmore R, Fennell E, Heilman K M (1994) Planum temporale asymmetry and language dominance. Neuropsychologia 32:1225-1231.

Foundas A L, Leonard C M, Heilman K M (1995) Morphological cerebral asymmetries and handedness: the pars triangularis and planum temporale. Arch Neurol 52:501-508.

Heinrichs R W (2001) In Search of Madness: Schizophrenia and Neuroscience. New York: Oxford.

Hollingshead A B (1975) Four factor index of social skills. New Haven: Yale University.

Ide A, Rodriguez E, Zaidel E, Aboitiz F (1996) Bifurcation patterns in the human sylvian fissure: hemispheric and sex differences. Cereb Cortex 6:717-725.

Javitt D C, Shelley, A. M., Silipo, G., Lieberman, J. A. (2000) Deficits in auditory and visual context-dependent processing in schizophrenia: defining the pattern. Arch Gen Psychiatry 57:1131-1137.

Kay S R, Opler L A, Fiszbein A (1992) Positive and Negative Syndrome Scale (PANSS +/−) Manual. North Tonawanda, N.Y.: Multi-Health Systems Inc.

Leonard C M (1996) Structural variation in the developing and mature brain: Noise or signal. In: Developmental neuroimaging: Mapping the development of brain and behavior (Thatcher R W, Lyon G R, Rumsey J, Krasnegor N, eds). New York: Academic Press.

Leonard C M, Puranik C, Kuldau J M, Lombardino L J (1998) Normal variation in the frequency and location of human auditory cortex landmarks: Heschl's gyrus: Where is it? Cereb Cortex 8:397-406.

Leonard C M, Eckert M A, Lombardino L J, Givens B K, Eden G F (2001a) Two anatomical phenotypes for reading impairment. J Cogn Neurosci 12(abs).

Leonard C M, Kuldau J M, Voeller K K S, Honeyman J C, Agee O F, Mancuso A A (1993) MRI studies of gyral anatomyin neuropsychiatry. APA New Research Presentations 115.

Leonard C M, Eckert M A, Lombardino L J, Oakland T, Kranzler J, Mohr C M, King W M, Freeman A J (2001b) Anatomical risk factors for phonological dyslexia Cereb Cortex 11:148-157.

Leonard C M, Kuldau J M, Breier J I, Zuffante P A, Gautier E R, Heron D C, Lavery E M, Packing J, Williams S A, DeBose C A (1999) Cumulative effect of anatomical risk factors for schizophrenia: An MRI study. Biol Psychiatry 46:374-382.

Leopold D A, Logothetis N K (1996) Activity changes in early visual cortex reflect monkeys' percepts during binocular rivalry. Nature 379:549-553.

Levelt W J M (1965) On binocular rivalry. The Hague: Mouton: Assen: Van Gorcum.

Lipp O, Krrinitzky, S P (1998) The effect of repeated prepulse and reflex stimulus presentations on startle prepulse inhibition. Biol Psychol 47:65-76.

Livingstone M S, Rosen G D, Drislane F W, Galaburda A (1991) Physiological and anatomical evidence for a magnocellular deficit in developmental dyslexia. Proceedings of the National Academy of Sciences 88:7943-7947.

Logothetis N K, Leopold D A, Sheinberg D L (1996a) What is rivaling during binocular rivalry? Nature 380:621-624.

Logothetis N K, Leopold D A, Sheinberg D L (1996b) What is rivalling during binocular rivalry? Nature 380:621-624.

Lumer E, Friston, K J, Rees, G (1998) Neural Correlates of perceptual rivalry in the human brain. Science 280:1930-1934.

Miller S M, Liu G B, Ngo T T, Hooper G, Riek S, Carson R G, Pettigrew J D (2000) Interhemispheric switching mediates perceptual rivalry. Curr Biol 10:383-392.

Pettigrew J D (2001) Searching for the switch: Neural bases of perceptual rivalry alternations. Brain and Mind.

Pettigrew J D, Miller S M (1998) A 'sticky' interhemispheric switch in bipolar disorder? Proceedings of the Royal Society of London B 265:2141-2148.

Polonsky A, Blake, R, Braun, J, Heeger, D J (2000) Neuronal activity in human primary visual cortex correlates with perception during binocular rivalry. Nat Neurosci 3:1153-1159.

Rumsey J M (1998) Brain imaging of reading disorders. Journal of the American Academy of Adolescent Psychiatry 37:12.

Sheinberg D L, Logothetis, N K (2001) Noticing familiar objects in real world scenes: the role of temporal cortical neurons in natural vision. J Neurosci 21:1340-1350.

Siegel S (1956) Nonparametric statistics for the behavioral sciences. New York: McGraw Hill.

Silver M, Leopold, N K, Logothetis, N K (2001) Grouping and segmentation in binocular rivalry. Perception.

Srinivasan R, Russell, D P, Edelman, G M, Tononi, G (1999) Increased synchronization of neuromagnetic responses during conscious perception. J Neurosci 19:5435-5448.

Talairach J, Tournoux, P (1988) Co-Planar Stereotaxic Atlas of the Human Brain.: Thieme Medical Publishers.

Tong F, Engel, S A (2001) Interocular rivalry revealed in the human cortical blind-spot representation. Nature 411:195-199.

Tong F, Nakayama, K., Vaughan, J. T., Kanwisher, N. (1998) Binocular rivalry and visual awareness in human extrastriate cortex. Neuron 21:753-759.

Weickert T W, Goldberg T E, Gold J M, Bigelow L B, Egan M F, Weinberger D R (2000) Cognitive impairments in patients with schizophrenia displaying preserved and compromised intellect. Arch Gen Psychiatry 57:907-913.

Witelson S F, Kigar D (1992) Sylvian fissure morphology and asymmetry in men and women: bilateral differences in relation to handedness in men. J Comp Neurol 323: 326-340.

Woodcock R W (1987) Woodcock Reading Mastery Tests, Revised. Circle Pines Minn.: American Guidance Service.

Woodcock R W, Mather N (1989) WJ-R Tests of Cognitive Ability-Standard and Supplemental Batteries: Examiner's Manual. In: Woodcock-Johnson Psycho-Educational Battery-Revised (Woodcock R W, Johnson M B, eds). Chicago: Riverside Publishing.

Andreason, N. (1984). *Schedule for Assessment of Positive Symptoms*. Iowa City, Iowa.

Best, M. and J. Demb (1999). "Normal planum temporale asymmetry in dyslexics with a magnocellular deficit." *Neuroreport* 10: 607-612.

Briggs, G. G. and R. D. Nebes (1974). "Patterns of hand preference in a student population." *Cortex* 11: 230-238.

Campain, R. and J. Minckler (976). "A note on the gross configurations of the human auditory cortex." *Brain and Language* 3: 318-323.

Carroll, J. B. (1993). *Human cognitive abilities: A survey of factor, analytic studies*. Cambridge, Cambridge University Press.

First, M. B., Spitzer, R. L., Gibbon, M. and Williams, J. B. W. (1996). *Structured clinical interview for DSM-IV Axis I disorders—Patient edition (SCID-I/P, Version 2.0)* Biometrics Research Department New York State Psychiatric Institute 722 West 168th St NY N.Y. 10032.

Goldman-Rakic, P. S. (1987). "Development of cortical circuitry and cognitive function." *Child Development* 58: 642-691.

Goldman-Rakic, P. S. and L. D. Selemon (1997). "Functional and anatomical aspects of prefrontal pathology in schizophrenia." *Schizophrenia Bulletin* 23: 437-458.

Hollingshead, A. B. (1975). *Four factor index of social skills*. New Haven, Yale University.

Jones, P., B. Rodgers, et al. (1994). "Child developmental risk factors for adult schizophrenia in the British 1946 birth cohort." *Lancet* 344: 1398-1402.

Kay, S. R., L. A. Opler, et al. (1992). *Positive and Negative Syndrome Scale (PANSS +/−) Manual*. North Tonawanda, N.Y., Multi-Health Systems Inc.

Lane, A., A. Kinsella, et al. (1997). "The anthropometric assessment of dysmorphic features in schizophrenia as an index of its developmental origins." *Psychological Medicine* 27(5): 1155-64.

Leonard, C. M., M. A. Eckert, et al. (2001). "Two anatomical phenotypes for reading impairment." *Journal of Cognitive Neuroscience* 12(abs).

Leonard, C. M., M. A. Eckert, et al. (2001). "Anatomical risk factors for phonological dyslexia." *Cerebral Cortex* 11: 148-157.

Leonard, C. M., J. M. Kuldau, et al. (1999). "Cumulative effect of anatomical risk factors for schizophrenia: An MRI study." *Biological Psychiatry* 46: 374-382.

Leonard, C. M., C. Puranik, et al. (1998). "Normal variation in the frequency and location of human auditory cortex landmarks: Heschl's gyrus: Where is it?" *Cerebral Cortex* 8: 397-406.

Leonard, C. M., K. S. Voeller, et al. (1993). "Anomalous cerebral structure in dyslexia revealed with magnetic resonance imaging." *Archives of Neurology* 50: 461-469.

Leopold, D. A. and N. K. Logothetis (1996). "Activity changes in early visual cortex reflect monkeys' percepts during binocular rivalry." *Nature* 379(6565): 549-53.

Leopold, D. A. and N. K. Logothetis (1999). "Multistable phenomena: changing views in perception." *Trends Cogn Sci* 3(7): 254-264.

Lieberman, J., D. Jody, et al. (1993). "Time course and biologic correlates of treatment response in first episode schizophrenia." *Archives of General Psychiatry* 50: 369-376.

Lipska, B. K., G. E. Jaskiw, et al. (1993). "Postpubertal emergence of hyperresponsiveness to stress and to amphetamine after neonatal excitotoxic hippocampal damage; A potential animal model of schizophrenia." *Neuropsychopharmacology* 9: 67-75.

Liu, Y., Y. Pu, et al. (2000). "The human red nucleus and lateral cerebellum in supporting roles for sensory information processing." *Hum Brain Mapp* 10(4): 147-59.

Logothetis, N. K., D. A. Leopold, et al. (1996). "What is rivalling during binocular rivalry?" *Nature* 380(6575): 621-4.

Meltzer, H. Y., J. Rabinowitz, et al. (1997). "Age of onset and gender of schizophrenic patients in relation to neuroleptic resistance." *American Journal of Psychiatry* 154: 475-482.

Miller, S. M., G. B. Liu, et al. (2000). "Interhemispheric switching mediates perceptual rivalry." *Current Biology* 10: 383-392.

National Institute of Mental, H. (1975). "Abnormal Involuntary Movement Scale (AIMS)." *Early Clinical Drug Evaluation Unit Intercom* 4: 3-6.

Olney, J. W. and N. B. Farber (1995). "Glutamate receptor dysfunction and schizophrenia." *Archives of General Psychiatry* 52: 998-1007.

Pearlson, G. D., D. J. Garbacz, et al. (1984). "Lateral ventricular enlargement associated with persistent unemployment and negative symptoms in both schizophrenia and bipolar disorder." *Psychiatry Research* 12: 1-19.

Penhune, V. B., R. J. Zatorre, et al. (1996). "Interhemispheric anatomical differences in human primary auditory cortex; probabilistic mapping and volume measurement from magnetic resonance scans." *Cerebral Cortex* 6: 661-672.

Pettigrew, J. D. and S. M. Miller (1998). "A 'sticky' interhemispheric switch in bipolar disorder?" *Proceedings of the Royal Society of London B* 265: 2141-2148.

Shannahoff-Khalsa, D. S. and F. E. Yates (2000). "Ultradian sleep rhythms of lateral EEG, autonomic, and cardiovascular activity are coupled in humans." *Int J Neurosci* 101(1-4): 21-43.

Sokolski, K. N., J. L. Cummings, et al. (1994). "Effects of substance abuse on hallucination rates and treatment responses in chronic psychiatric patients." *Journal of Clinical Psychiatry* 55: 380-387.

Stevens, J. (1997). "Anatomy of schizophrenia revisited." *Schizophrenia Bulletin* 23: 373-383.

Stevens, J. R. (1992). "Abnormal reinnervation as a basis for schizophrenia: a hypothesis." *Archives of General Psychiatry* 49: 238-243.

Talairach, J. and P. Toumoux (1988). *Coplanar stereotaxic atlas of the human brain: Three-dimensional proportional system: An approach to cerebral imaging*. New York, Thieme.

Tononi, G. and G. Edelman (2000). "Schizophrenia and the mechanisms of conscious integration." *Brain Research Reviews* 31: 391-400.

Weickert, T. W., T. E. Goldberg, et al. (2000). "Cognitive impairments in patients with schizophrenia displaying preserved and compromised intellect." *Archives of General Psychiatry* 57: 907-913.

Weinberger, D. R. (1995). Schizophrenia as a neurodevelopmental disorder. *Schizophrenia*. S. R. Hirsch and D. R. Weinberger. Oxford, Blackwell Science Ltd: 293-323.

White K., K. J., Leonard C., Maron L., Bengtson M., Ricciuti N., Hahn R., Pettigrew., et al. (2001). "www.psych.ufl.edu/~white/CNSposter.ppt] Schizophrenics exhibit abnormal binocular rivalry." *Journal of Cognitive Neuroscience* Supplement: 106.

Woodcock, R. W. (1987). *Woodcock Reading Mastery Tests, Revised*. Circle Pines Minn., American Guidance Service.

Woodcock, R. W. and M. B. Johnson (1989). *Woodcock-Johnson Psycho-Education Battery-Revised*. Chicago Ill., Riverside Publishing Co.

Xiong, J., Gao, J-H, Lancaster J L, Fox, P T (2000). "Clustered pixels analysis for functional MRI activation studies of the human brain." *Human Brain Mapping* 3: 287-301147-159.

TABLE 1

|  | Control | Patient | p < (t test) |
|---|---|---|---|
| Sex (M/F) | 20/4 | 16/2 |  |
| Age | 45 (8) | 41 (10) | NS |
| Hand Dominance | 0.63 (.5) | 0.64 (.5) | NS |
| Parental SES | 42 (9) | 38 (14) | NS |
| Woodcock-Johnson-R |  |  |  |
| Broad Cognitive Ability | 115 (14) | 93 (12) | .0001 |
| Vocabulary | 111 (14) | 92 (17) | .0004 |
| Nonverbal Reasoning | 109 (14) | 100 (13) | .0003 |
| Processing Speed | 108 (14) | 88 (10) | .0001 |
| PANSS Factors |  |  |  |
| Reality Distortion | 3.1 (.5) | 10.5 (3.7) | .0001 |
| Poverty | 5.1 (.25) | 11.5 (4.1) | .0001 |
| Disorganization | 4.1 (.25) | 10.9 (2.6) | .0001 |

TABLE 2

|  |  | Dichoptic Stimulus Alternation Rate (Hz) | | | | |
|---|---|---|---|---|---|---|
|  |  | 0 | 3.75 | 7.5 | 15 | 30 |
| Control | q1 | 1.54 | 0.22 | 0.13 | 0.03 | 0.02 |
|  | median | 2.4 | 0.32 | 0.15 | 0.08 | 0.06 |
|  | q3 | 2.6 | 0.41 | 0.19 | 0.15 | 0.12 |
| Patient | q1 | 1.85 | 0.31 | 0.21 | 0.18 | 0.25 |
|  | median | 3.2 | 0.7 | 0.65 | 0.56 | 0.54 |
|  | q3 | 4 | 1.1 | 1.28 | 1.56 | 1.45 |
| Chi square |  | 5.2 | 6.2 | 13.2 | 11.9 | 15.0 |
| P< |  | .03 | .015 | .0005 | .001 | .0001 |

TABLE 3

|  |  |  | Likelihood Ratio Correct/Wrong | |
|---|---|---|---|---|
| Diagnosis | Rivalry | n | Mean | Std. Dev. |
| Control | No | 14 | 8.6 | 4.4 |
|  | Yes | 4 | 9 | 4.5 |

TABLE 3-continued

| Patient | No | 8 | 3.8 | 3.1 |
|---|---|---|---|---|
|  | Yes | 16 | 2.9 | 1.4 |
| Statistical Analysis | df | F | p | |
| Model | 3.36 | 9.13 | .0001 | |
| Diagnosis | 1 | 21.05 | .0001 | |
| Rivalry | 1 | 0.04 | .84 | |
| Interaction | 1 | 0.31 | .56 | |

TABLE 4

| | Number of rivalry reports at rapid DSA rates | | | | |
|---|---|---|---|---|---|
| | 0 | 1 | 2 | 3 | 4 |
| Control | 14 | 3 | 0 | 1 | 0 |
| Schizophrenia | 8 | 5 | 5 | 3 | 3 |

TABLE 5

| Characteristic | A | B |
|---|---|---|
| Slow rivalry alternation with 30 dichoptic reversal/sec stimulation | No | Yes |
| Rivalrous responses in traditional rivalry unusually frequent at 0.25 sec | No | Yes |
| Crosshatch responses in traditional rivalry are distributed like controls' | No | Yes |
| Unusually small size of plana temporale ($<2$ cm$^2$) | 0/10 | 4/6 |
| Poorer reading, oral language, and short term memory abilities | No | Yes |

The invention claimed is:

1. A method for diagnosing schizophrenia, schizophrenic disorder subtype, or predisposition thereto in a test subject, said method including the steps of:
    (a) measuring an interhemispheric switch rate of the test subject; and
    (b) comparing the measured switch rate with a corresponding reference switch rate to diagnose presence or absence of schizophrenia, schizophrenia disorder subtype or predisposition thereto;
wherein said schizophrenia or schizophrenia disorder subtype is diagnosed when the measured switch rate is above 2.0 Hz.

2. The method of claim 1 wherein the interhemispheric switch rate is determined by measuring a rate of perceptual rivalry in the test subject.

3. The method of claim 2 wherein the rate of perceptual rivalry is determined by measuring a rate of binocular rivalry.

4. The method of claim 2 wherein the rate of perceptual rivalry is measured by:—
    (i) displaying at least one image to the test subject, wherein the at least one image invokes perceptual alternation;
    (ii) signalling respective incidences of perceptual alternation in the test subject during a predetermined period to provide a number of signals; and
    (iii) dividing the number of signals by the predetermined period to provide the rate of perceptual rivalry.

5. The method of claim 1 wherein the schizophrenia disorder subtype is diagnosed when the measured switch rate is in a range from 2.0 Hz to 10.0 Hz.

6. The method of claim 5 wherein the measured switch rate is in a range from 3.3 Hz to 5.0 Hz.

7. A method for diagnosing schizophrenia, schizophrenic disorder subtype, or predisposition thereto in a test subject, said method including the steps of:
    (1) measuring binocular rivalry rate in the subject; and
    (2) comparing said measured binocular rivalry rate with a corresponding reference binocular rivalry rate to diagnose presence or absence of schizophrenia, schizophrenia disorder subtype, or predisposition thereto,
    wherein said schizophrenia or schizophrenia disorder subtype is diagnosed when the measured binocular rivalry rate is above 2.0 Hz.

8. The method of claim 7 wherein the schizophrenia disorder subtype is diagnosed when the measured binocular rivalry rate is in a range from 2.0 Hz to 10.0 Hz.

9. The method of claim 8 wherein the measured binocular rivalry rate is in a range from 3.3 Hz to 5.0 Hz.

10. A method for diagnosing a schizophrenic disorder subtype or predisposition thereto in a test subject, said method including the steps of:
    (A) measuring a dichoptic reversal rate whereby the subject is capable of perceiving that binocular rivalry persists; and
    (B) comparing said measured dichoptic reversal rate with a corresponding reference dichoptic reversal rate to diagnose presence or absence of a schizophrenic disorder subtype or predisposition thereto.

11. The method of claim 10 wherein diagnosis of the schizophrenic disorder subtype or predisposition thereto is indicated when the subject is capable of perceiving binocular rivalry when the measured dichoptic reversal rate is greater than 4.0 Hz.

12. The method of claim 11 wherein the measured dichoptic reversal rate is greater than 15.0 Hz.

13. The method of claim 12 wherein the measured dichoptic reversal rate is greater than 30.0 Hz.

14. A process for identifying one or more genetic markers associated with schizophrenia, or schizophrenic disorder subtype, said process including the steps of:
    (I') testing respective members of one or more pedigrees affected by schizophrenia, or schizophrenic disorder subtype, using the method of claim 1, claim 5, or claim 9;
    (II') identifying members having schizophrenia, or schizophrenic disorder subtype or predisposition thereto; and
    (III') conducting genetic linkage analysis on the identified members to identify the or each genetic marker associated with schizophrenia, or schizophrenic disorder subtype.

15. A genetic marker identified according to the process of claim 14.

16. A method of treating a patient with schizophrenia or a schizophrenic disorder subtype including the steps of:—
    (I) measuring an interhemispheric switch rate of the patient;
    (II) comparing said measured interhemispheric switch rate with a range of reference interhemispheric switch rates associated with schizophrenia or schizophrenia disorder subtype, wherein said diagnosis of schizophrenia, schizophrenia disorder subtype, or a predisposition thereto is indicated when the measured interhemispheric switch rate is above 2.0 Hz; and (III) administering to said patient a pharmaceutically-effective dosage of a drug for treating schizophrenia or a schizophrenic disorder subtype, when said measured interhemispheric switch rate is in said range.

17. The method of claim 16 wherein diagnosis of the schizophrenic disorder subtype or predisposition thereto is indicated when the measured interhemispheric switch rate is in a range from 2.0 Hz to 10.0 Hz.

18. The method of claim 17 wherein the measured interhemispheric switch rate is in a range from 3.3 Hz to 5.0 Hz.

19. A method of treating a patient with schizophrenia or a schizophrenic disorder subtype including the steps of:—
   (a') measuring a dichoptic reversal rate whereby the subject is capable of perceiving that binocular rivalry persists;
   (b') comparing said measured dichoptic reversal rate with a corresponding reference dichoptic reversal rate to diagnose presence or absence of a schizophrenic disorder subtype or predisposition thereto; and
   (c') administering to said patient a pharmaceutically-effective dosage of a drug for treating schizophrenia or a schizophrenic disorder subtype, when said measured dichoptic reversal rate is in said range.

20. The method of claim 19 wherein the drug is administered to the patient when the patient is capable of perceiving binocular rivalry when the measured dichoptic reversal rate is above 4.0 Hz.

21. The method of claim 20 wherein the measured dichoptic reversal rate is above 15.0 Hz.

22. The method of claim 21 wherein the measured dichoptic reversal rate is above 30.0 Hz.

23. A method for diagnosing schizophrenia, schizophrenic subtype or predisposition thereto in a test subject, said method including the steps of:
   (i') displaying at least one image to the test subject, wherein the at least one image invokes perceptual alternation by dichoptic reversal;
   (ii') scanning the brain of the test subject during perceptual alternation;
   (iii') detecting an anatomical structure in the brain of the test subject; and
   (iv') comparing the detected anatomical structure with a corresponding reference anatomical structure to diagnose presence or absence of schizophrenia or schizophrenic subtype.

24. The method of claim 23 wherein said scanning is by functional MRI, positron emission tomography, MEG or multi-electrode VEP.

* * * * *

UNITED STATES PATENT AND TRADEMARK OFFICE
CERTIFICATE OF CORRECTION

PATENT NO. : 7,338,455 B2 Page 1 of 1
APPLICATION NO. : 10/491020
DATED : March 4, 2008
INVENTOR(S) : Keith D. White et al.

It is certified that error appears in the above-identified patent and that said Letters Patent is hereby corrected as shown below:

Column 4,
Line 35, delete "In fourth" and insert --In a fourth--.
Line 60, delete "In fifth" and insert --In a fifth--.

Column 5, line 63, delete "In a eighth" and insert --in an eighth--.

Column 7,
Line 24, delete "patter" and insert --pattern--.
Line 24, delete "may also typical" and insert --may also be typical--.

Column 10, line 10, delete "surprising" and insert --surprisingly--.

Column 14, line 22, delete "is in the range of between".

Column 27, line 41, delete "were" and insert --was--.

Column 31, line 8, delete "anatomyin" and insert --anatomy in--.

Column 34,
Line 51 (Table 2), move "Control" to read --Control median--.
Line 53 (Table 2), move "Patient" to read --Patient median--.

Signed and Sealed this

Second Day of September, 2008

JON W. DUDAS
*Director of the United States Patent and Trademark Office*